US011491221B2

(12) United States Patent
Fan et al.

(10) Patent No.: US 11,491,221 B2
(45) Date of Patent: Nov. 8, 2022

(54) IMMUNOSUPPRESSIVE COMPOSITION FOR USE IN TREATING IMMUNOLOGICAL DISORDERS

(71) Applicant: Singapore Health Services Pte Ltd, Singapore (SG)

(72) Inventors: Xiubo Fan, Singapore (SG); William Ying Khee Hwang, Singapore (SG); Hsiu Ling Low, Singapore (SG); Julian Thumboo, Singapore (SG); Chin Teck Ng, Singapore (SG)

(73) Assignees: Singapore Health Services Pte Ltd, Singapore (SG); Singapore General Hospital, Singapore (SG)

( * ) Notice: Subject to any disclaimer, the term of this patent is extended or adjusted under 35 U.S.C. 154(b) by 651 days.

(21) Appl. No.: 16/326,417

(22) PCT Filed: Aug. 18, 2017

(86) PCT No.: PCT/SG2017/050408
§ 371 (c)(1),
(2) Date: Feb. 19, 2019

(87) PCT Pub. No.: WO2018/034620
PCT Pub. Date: Feb. 22, 2018

(65) Prior Publication Data
US 2021/0252140 A1    Aug. 19, 2021

(30) Foreign Application Priority Data

Aug. 19, 2016    (SG) .......................... 10201606949Q

(51) Int. Cl.
*A61K 39/395* (2006.01)
*A61K 38/19* (2006.01)
*A61P 37/06* (2006.01)

(52) U.S. Cl.
CPC .......... *A61K 39/3955* (2013.01); *A61K 38/19* (2013.01); *A61K 38/195* (2013.01); *A61P 37/06* (2018.01)

(58) Field of Classification Search
None
See application file for complete search history.

(56) References Cited

U.S. PATENT DOCUMENTS

2007/0071675 A1    3/2007  Wu et al.
2011/0280800 A1   11/2011  Wu et al.

FOREIGN PATENT DOCUMENTS

| JP | 2013-18756 A | 1/2013 |
| WO | WO-93/17698 A1 | 9/1993 |
| WO | WO-02/43758 A2 | 6/2002 |
| WO | WO-02/081521 A2 | 10/2002 |
| WO | WO-2006/081139 A2 | 8/2006 |
| WO | WO-2010/086854 A1 | 8/2010 |
| WO | WO-2011/072119 A2 | 6/2011 |
| WO | WO-2013/068902 A1 | 5/2013 |
| WO | WO-2015/133668 A1 | 9/2015 |

OTHER PUBLICATIONS

Supplementary European Search Report in EP Application No. 17841766.3 dated Jan. 24, 2020, 6 pages.
Shi et al., "Allogeneic Transplantation of Umbilical Cord-derived Mesenchymal Stem Cells for Diffuse Alveolar Hemorrhage in Systemic Lupus Erythematosus", Clin Rheumatol, 31, 2012, pp. 841-846.
Search Report and Written Opinion in International Application No. PCT/SG2017/050408 dated Nov. 15, 2017, 15 pages.
Bassi et al., "Exploring the Role of Soluble Factors Associated with Immune Regulatory Properties of Mesenchymal Stem Cells", Stem Cell Rev and Rep, vol. 8, No. 2, Sep. 1, 2011, pp. 329-342.
Fan et al., "A Two Factor-cocktail: Potential Substitute for Mesenchymal Stromal Cells in Suppressing Graft Versus Host Disease", European Journal of Immunology, vol. 46, No. Supplement 1, Aug. 19, 2016, 1 page.
Fan et al., "Application of a Mesenchymal Stromal Cell-Derived Two-factor Cocktail in Graft Versus Host Disease Therapy", Cytotherapy, vol. 19, No. 5 Supplement, 1 page, May 2017.
Sun et al., "Substitute Mesenchymal Stromal Cells Therapy in Graft Versus Host Disease With a Chemically Defined Cocktail", J. Clin Cell Immunol, vol. 8, No. 3 Supplement, p. 78 ; Jul. 2017.
Introna et al., "Treatment of graft versus host disease with mesenchymal stromal cells: a phase I study on 40 adult and pediatric patients", Biology of Blood and Marrow Transplantation: Journal of the American Society for Blood and Marrow Transplantation 20, 2014, pp. 375-381.
Baron et al., "Cotransplantation of mesenchymal stem cells might prevent death from graft-versus-host disease (GVHD) without abrogating graft-versus-tumor effects after HLA-mismatched allogeneic transplantation following nonmyeloablative conditioning", Biology of Blood and Marrow Transplantation: Journal of the American Society for Blood and Marrow Transplantation 16, 2010, pp. 838-847.
Arima et al., "Single intra-arterial injection of mesenchymal stromal cells for treatment of steroid-refractory acute graft-versus-host disease: a pilot study", Cytotherapy 12, 2010, pp. 265-268.
Zhou et al., "Efficacy of bone marrow-derived mesenchymal stem cells in the treatment of sclerodermatous chronic graft-versus-host disease: clinical report", Biology of Blood and Marrow Transplantation: Journal of the American Society for Blood and Marrow Transplantation, 16, 2010, pp. 403-412.
Xiong et al., "Mesenchymal stem cells versus mesenchymal stem cells combined with cord blood for engraftment failure after autologous hematopoietic stem cell transplantation: a pilot prospective, open-label, randomized trial", Biology of Blood and Marrow Transplantation: Journal of the American Society for Blood and Marrow Transplantation, 20, 2014, pp. 236-242.

(Continued)

*Primary Examiner* — Bridget E Bunner
*Assistant Examiner* — Fozia M Hamud
(74) *Attorney, Agent, or Firm* — Marshall, Gerstein & Borun LLP

(57) ABSTRACT

A pharmaceutical composition comprising at least one antibody and at least one mesenchymal stromal cell-derived protein, use of the pharmaceutical composition for treating immunological diseases, for example alloimmune and autoimmune diseases, and use of the pharmaceutical composition for immunomodulation.

6 Claims, 15 Drawing Sheets

(56) References Cited

OTHER PUBLICATIONS

Sanchez-Guijo et al., "Sequential third-party mesenchymal stromal cell therapy for refractory acute graft-versus-host disease", Biology of Blood and Marrow Transplantation, 20, 2014, pp. 1580-1585.

Wang et al., "Allogeneic mesenchymal stem cell transplantation in severe and refractory systemic lupus erythematosus: 4 years of experience", Cell transplantation vol. 22, 2013, pp. 2267-2277.

Wang et al., "Umbilical cord mesenchymal stem cell transplantation in active and refractory systemic lupus erythematosus: a multicenter clinical study", Arthritis Research & Therapy, 16:R79, 2014, 14 pages.

Sun et al., "Umbilical cord mesenchymal stem cell transplantation in severe and refractory systemic lupus erythematosus", Arthritis and Rheumatism, vol. 62, No. 8, 2010, pp. 2467-2475.

Li et al., "Mesenchymal SCT ameliorates refractory cytopenia in patients with systemic lupus erythematosus", Bone Marrow Transplantation, 48, 2013, pp. 544-550.

Woodworth et al., "Safety and feasibility of umbilical cord mesenchymal stem cells in treatment-refractory systemic lupus erythematosus nephritis: time for a double-blind placebo-controlled trial to determine efficacy", Arthritis Research & Therapy, 16:113, 2014, 3 pages.

Cai et al., "Umbilical Cord Mesenchymal Stromal Cell With Autologous Bone Marrow Cell Transplantation in Established Type 1 Diabetes: A Pilot Randomized Controlled Open-Label Clinical Study to Assess Safety and Impact on Insulin Secretion", Diabetes Care, vol. 39, 2016, pp. 149-157.

Forbes et al., "A phase 2 study of allogeneic mesenchymal stromal cells for luminal Crohn's disease refractory to biologic therapy", Clinical Gastroenterology and Hepatology, 12, 2014, pp. 64-71.

Walsh et al., "Infection with a helminth parasite attenuates autoimmunity through TGF-beta-mediated suppression of Th17 and Th1 responses", The Journal of Immunology, 183, 2009, pp. 1577-1586.

Di Nicola et al., "Human bone marrow stromal cells suppress T-lymphocyte proliferation induced by cellular or nonspecific mitogenic stimuli", Blood, vol. 99, No. 10, 2002, pp. 3838-3843.

Masteller et al., "Expansion of functional endogenous antigen-specific $CD4^+CD25^+$ regulatory T cells from nonobese diabetic mice", The Journal of Immunology, 175, 2005, pp. 3053-3059.

Aggarwal et al., "Human mesenchymal stem cells modulate allogeneic immune cell responses", Blood, vol. 105, No. 4, 2005, pp. 1815-1822.

Meisel et al., "Human bone marrow stromal cells inhibit allogeneic T-cell responses by indoleamine 2,3-dioxygenase-mediated tryptophan degradation", Blood 2004, vol. 103, No. 12, pp. 4619-4621.

Su et al., "Phylogenetic distinction of iNOS and IDO function in mesenchymal stem cell-mediated immunosuppression in mammalian species", Cell Death and Differentiation, 21, 2014, pp. 388-396.

Meisel et al., "Human but not murine multipotent mesenchymal stromal cells exhibit broad-spectrum antimicrobial effector function mediated by indoleamine 2,3-dioxygenase", Leukemia, 25, 2011, pp. 648-654.

Jui et al., "Autologous mesenchymal stem cells prevent transplant arteriosclerosis by enhancing local expression of interleukin-10, interferon-gamma, and indoleamine 2,3-dioxygenase", Cell Transplantation, vol. 21, 2012, pp. 971-984.

Ge et al., "Regulatory T-cell generation and kidney allograft tolerance induced by mesenchymal stem cells associated with indoleamine 2,3-dioxygenase expression", Transplantation, vol. 90, No. 12, 2010, pp. 1312-1320.

Nemeth et al., "Bone marrow stromal cells attenuate sepsis via prostaglandin $E_2$-dependent reprogramming of host macrophages to increase their interleukin-10 production", Nature Medicine, 15(1), 2009, pp. 42-49.

Ren et al., "Mesenchymal stem cell-mediated immunosuppression occurs via concerted action of chemokines and nitric oxide", Cell Stem Cell, 2, 2008, pp. 141-150.

Oh et al., "Intravenous mesenchymal stem cells prevented rejection of allogeneic corneal transplants by aborting the early inflammatory response", Molecular Therapy: The Journal of the American Society of Gene Therapy, vol. 20, No. 11, 2012, pp. 2143-2152.

Mougiakakos et al., "The impact of inflammatory licensing on heme oxygenase-1-mediated induction of regulatory T cells by human mesenchymal stem cells", Blood, vol. 117, No. 18, 2011, pp. 4826-4835.

Liang et al., "Mesenchymal stromal cells expressing heme oxygenase-1 reverse pulmonary hypertension", Stem Cells 29(1), 2011, pp. 99-107.

Hou et al., "The effect of heme oxygenase-1 complexed with collagen on MSC performance in the treatment of diabetic ischemic ulcer", Biomaterials, 34, 2013, pp. 112-120.

Hall et al., "Mesenchymal stromal cells improve survival during sepsis in the absence of heme oxygenase-1: the importance of neutrophils", Stem Cells 31(2), 2013, pp. 397-407.

Burgess et al., "Epoxyeicosatrienoic acids and heme oxygenase-1 interaction attenuates diabetes and metabolic syndrome complications", Prostaglandins & Other Lipid Mediators, 97(0), 2012, 34 pages.

Gieseke et al., "Human multipotent mesenchymal stromal cells use galectin-1 to inhibit immune effector cells", Blood, vol. 116, No. 19, 2010, pp. 3770-3779.

Yang et al., "Enhancement of the immunosuppressive effect of human adipose tissue-derived mesenchymal stromal cells through HLA-G1 expression", Cytotherapy, 14, 2012, pp. 70-79.

Selmani et al., "HLA-G is a crucial immunosuppressive molecule secreted by adult human mesenchymal stem cells", Transplantation, vol. 87, No. 9S, 2009, pp. S62-S66.

Montespan et al., "Osteodifferentiated mesenchymal stem cells from bone marrow and adipose tissue express HLA-G and display immunomodulatory properties in HLA-mismatched settings: implications in bone repair therapy", Journal of Immunology Research, Article ID 230346, 2014, 10 pages.

Fan et al., "Mesenchymal stromal cell supported umbilical cord blood ex vivo expansion enhances regulatory T cells and reduces graft versus host disease", Cytotherapy, 15, 2013, pp. 610-619.

Beyrau et al., "Neutrophil heterogeneity in health and disease: a revitalized avenue in inflammation and immunity", Open Biology, 120134, 2012, 10 pages.

Hotchkiss et al., "The sepsis seesaw: tilting toward immunosuppression", Nature Medicine, 15(5), 2009, pp. 496-497.

Kamp et al., "Human suppressive neutrophils $CD16^{bright}/CD62L^{dim}$ exhibit decreased adhesion", Journal of Leukocyte Biology, vol. 92, 2012, pp. 1011-1020.

Pillay et al., "A subset of neutrophils in human systemic inflammation inhibits T cell responses through Mac-1", The Journal of Clinical Investigation, vol. 122, No. 1, 2012, pp. 327-336.

Forssmann et al., "Eotaxin-2, a novel CC chemokine that is selective for the chemokine receptor CCR3, and acts like eotaxin on human eosinophil and basophil leukocytes", J Exp Med., vol. 185, No. 12, Jun. 16, 1997, pp. 2171-2176.

Eum et al., "Inhibition of allergic airways inflammation and airway hyperresponsiveness in mice by dexamethasone: role of eosinophils, IL-5, eotaxin, and IL-13", The Journal of Allergy and Clinical Immunology, vol. 111, No. 5, 2003, pp. 1049-1061.

Dent et al., "Contribution of eotaxin-1 to eosinophil chemotactic activity of moderate and severe asthmatic sputum", American Journal of Respiratory and Critical Care Medicine, vol. 169, 2004, pp. 1110-1117.

Radinger et al., "Eotaxin-2 regulates newly produced and CD34 airway eosinophils after allergen exposure", The Journal of Allergy and Clinical Immunology, 113, 2004, pp. 1109-1116.

Lezcano-Meza et al., "Interleukin (IL)-4 and to a lesser extent either IL-13 or interferon-gamma regulate the production of eotaxin-2/CCL24 in nasal polyps", Allergy, 58, 2003, pp. 1011-1017.

Chae et al., "The suggestive association of eotaxin-2 and eotaxin-3 gene polymorphisms in Korean population with allergic rhinitis", Immunogenetics, 56, 2005, pp. 760-764.

De Corso et al., "Nasal lavage CCL24 levels correlate with eosinophils trafficking and symptoms in chronic sino-nasal eosinophilic inflammation", Rhinology, 49, 2011, pp. 174-179.

Cavallari et al., "Expression of RANTES, eotaxin-2, ICAM-1, LFA-1 and CCR-3 in chronic rhinosinusitis patients with nasal

(56) References Cited

OTHER PUBLICATIONS polyposis", Acta cirurgica brasileira / Sociedade Brasileira para Desenvolvimento Pesquisa em Cirurgia, vol. 27 (9), 2012, pp. 645-649.
De Corso et al., "Nasal fluid release of eotaxin-3 and eotaxin-2 in persistent sinonasal eosinophilic inflammation", International Forum of Allergy & Rhinology, vol. 4, No. 8, 2014, pp. 617-624.
Chen et al., "Increased serum levels of eotaxin in patients with inflammatory bowel disease," Scandinavian Journal of Gastroenterology, 36, 2001, pp. 515-520.
Manousou et al., "Increased expression of chemokine receptor CCR3 and its ligands in ulcerative colitis: the role of colonic epithelial cells in in vitro studies", Clinical and Experimental Immunology, 162, 2010, pp. 337-347.
Kagami et al., "Significant elevation of serum levels of eotaxin-3/CCL26, but not of eotaxin-2/CCL24, in patients with atopic dermatitis: serum eotaxin-3/CCL26 levels reflect the disease activity of atopic dermatitis", Clinical and Experimental Immunology, 134, 2003, pp. 309-313.
Owczarek et al., "Analysis of eotaxin 1/CCL11, eotaxin 2/CCL24 and eotaxin 3/CCL26 expression in lesional and non-lesional skin of patients with atopic dermatitis", Cytokine, 50, 2010, pp. 181-185.
Owczarek et al., "Relationship between serum eotaxins level and their genes expression in skin of atopic dermatitis patients", Annals of Allergy, Asthma & Immunology: Official Publication of the American College of Allergy, Asthma, & Immunology, 110, 2013, pp. 462-463.
Amerio et al., "Expression of eotaxin, interleukin 13 and tumour necrosis factor-alpha in dermatitis herpetiformis", The British Journal of Dermatology, 143, 2000, pp. 974-978.
Elsner et al., "Eotaxin-2 activates chemotaxis-related events and release of reactive oxygen species via pertussis toxin-sensitive G proteins in human eosinophils", Eur J Immunol., 28(7), Jul. 1998, pp. 2152-2158.
Simmons et al., "Potent inhibition of HIV-1 infectivity in macrophages and lymphocytes by a novel CCR5 antagonist", Science (New York, NY), vol. 276, 1997, pp. 276-279.
Nibbs et al., "C-C chemokine receptor 3 antagonism by the beta-chemokine macrophage inflammatory protein 4, a property strongly enhanced by an amino-terminal alanine-methionine swap", Journal of Immunology (Baltimore, Md : 1950), 164, 2000, pp. 1488-1497.
Supplementary European Search Report in EP Application No. 17841766 dated Mar. 3, 2020, 9 pages.
First Office Action for CN Application No. 201780062573.9 dated Aug. 3, 2022.

IMMUNOSUPPRESSIVE COMPOSITION FOR USE IN TREATING IMMUNOLOGICAL DISORDERS

CROSS-REFERENCE TO RELATED APPLICATIONS

This application claims the benefit of priority of Singapore provisional application No. 10201606949Q, filed 19 Aug. 2016, the contents of it being hereby incorporated by reference in its entirety for all purposes.

FIELD OF THE INVENTION

The present invention relates generally to the field of molecular biology. In particular, the present invention relates to compositions for the treatment of immunological disorders.

BACKGROUND OF THE INVENTION

Mesenchymal stromal cell (MSC) therapy has been shown to be effective in, for example, modulating immunological disorders, alloimmune disease (graft versus host disease (GVHD) after allogeneic hematopoietic cell transplantations) and autoimmune diseases systemic lupus erythematosus (SLE), lupus nephritis, type-I diabetes mellitus, systemic sclerosis, inflammatory bowel disease (IBD), Crohn's disease, etc.). However, MSC therapy trials still face challenges regarding unforeseen long-term complications, potential tumorigenicity and uncontrolled differentiation to unwanted cells or tissue types. Also, the use of human mesenchymal stromal cells raises the question of the equivalence of cells isolated from different sources and using different expansion methods.

Therefore, there is a need for a replacement for mesenchymal stromal cell (MSC) therapy for the treatment of immunological diseases.

SUMMARY

In one aspect, the present invention refers to a pharmaceutical composition comprising at least one antibody and at least one mesenchymal stromal cell-derived protein, wherein the antibody targets one or more of the cytokines selected from the group consisting of macrophage colony-stimulating factor (M-CSF), Interleukin-1beta (IL-1β), CCL-1 (I-309) and CCL24 (Eotaxin-2); wherein the mesenchymal stromal cell-derived protein is selected from the group consisting of PGE2 (prostaglandin E2), OPG, CCL7 (MCP-2), CCL8 (MCP-3), CCL20 (MIP-3α), CXCL5 (ENA-78), IL-10 and CXCL6 (GCP-2).

In one example, the present application discloses the pharmaceutical composition described herein, wherein the pharmaceutical composition is as shown in the table below:

| Composition | |
|---|---|
| C2a | CXCL5; anti-CCL1; anti-IL1b; anti-M-CSF; anti-CCL24 |
| C3a | CCL8; CCL7; OPG; IL-10; anti-CCL24 |
| C4a | CCL8; CCL7; OPG; IL-10; CXCL5; anti-CCL1; anti-IL1b; anti-M-CSF |
| C5a | CCL20; CXCL6; OPG; IL-10; anti-IL1b; anti-M-CSF |
| C6a | CCL20; CXCL6; OPG; IL-10; CXCL5; anti-CCL1; anti-CCL24 |
| C7a | CCL20; CXCL6; CCL8; CCL7; anti-IL1b; anti-M-CSF; anti-CCL24 |
| C8a | CCL20; CXCL6; CCL8; CCL7; CXCL5; anti-CCL1 |
| C9a | PGE2; CXCL6; CCL7; IL-10; anti-CCL1; anti-M-CSF |
| C10a | PGE2; CXCL6; CCL7; IL-10; CXCL5; anti-IL1b; anti-CCL24 |
| C11a | PGE2; CXCL6; CCL8; OPG; anti-CCL1; anti-M-CSF; anti-CCL24 |
| C12a | PGE2; CXCL6; CCL8; OPG; CXCL5; anti-IL1b |
| C13a | PGE2; CCL20; CCL7; OPG; anti-CCL1; anti-IL1b |
| C14a | PGE2; CCL20; CCL7; OPG; CXCL5; anti-M-CSF; anti-CCL24 |
| C15a | PGE2; CCL20; CCL8; IL-10; anti-CCL1; anti-IL1b; anti-CCL24 |
| C16a | PGE2; CCL20; CCL8; IL-10; CXCL5; anti-M-CSF |
| C17a | CXCL5; CXCL6; anti-CCL1; CCL20 |
| C18a | IL-10; OPG; anti-CCL1; CCL20 |
| C19a | IL-10; OPG; CXCL5; CXCL6 |
| C20a | anti-CCL24; OPG; CXCL6; CCL20 |
| C21a | anti-CCL24; OPG; CXCL5; anti-CCL1 |
| C22a | anti-CCL24; IL-10; CXCL6; anti-CCL1 |
| C23a | anti-CCL24; IL-10; CXCL5; CCL20 |
| C28a | anti-CCL1; anti-CCL24 |
| C29a | anti-CCL1; OPG |
| C30a | anti-CCL1; CXCL5 |
| C31a | anti-CCL24; OPG |
| C32a | anti-CCL24; CXCL5 |
| C33a | OPG; CXCL5 |
| C34a | anti-CCL1; anti-CCL24; OPG |
| C35a | anti-CCL1; anti-CCL24; CXCL5 |
| C36a | anti-CCL1; OPG; CXCL5 |
| C37a | anti-CCL24; OPG; CXCL5 |
| C38a | anti-CCL1; anti-CCL24; OPG; CXCL5 |

In another example, the present application discloses the pharmaceutical composition as described herein, wherein the pharmaceutical composition comprises CXCL5 and an anti-CCL24 antibody (C32a).

In yet another example, the present application discloses the pharmaceutical composition as described herein, wherein the antibody is present in a concentration of about 0.05 µg/ml to about 5 µg/ml.

In a further example, the present application discloses the pharmaceutical composition as described herein, wherein the antibody is present in a concentration of about 1 µg/ml or about 2 µg/ml.

In one example, the present application discloses the pharmaceutical composition as described herein, wherein the mesenchymal stromal cell-derived protein is present in a concentration of about 0.5 ng/ml to about 75 ng/ml.

In another example, the present application discloses the pharmaceutical composition as described herein, wherein the mesenchymal stromal cell-derived protein is present in a concentration of about 10 ng/ml or 50 ng/ml.

In another aspect, the present invention refers to a method of treating an immunological disorder, the method comprising administration of a pharmaceutical composition comprising at least one antibody and/or at least one mesenchymal stromal cell-derived protein, wherein the antibody targets one or more of the cytokines selected from the group consisting of macrophage colony-stimulating factor (M-CSF), Interleukin-1beta (IL-1β), CCL-1 (I-309) and CCL24 (Eotaxin-2); wherein the mesenchymal stromal cell-derived protein is selected from the group consisting of PGE2 (prostaglandin E2), OPG, CCL7 (MCP-2), CCL8 (MCP-3), CCL20 (MIP-3α), CXCL5 (ENA-78), IL-10 and CXCL6 (GCP-2).

In yet another aspect, the present invention refers to a method of modulating the immune system, the method comprising administration of a pharmaceutical composition as described herein.

In one example, the present application discloses the method described herein, wherein the pharmaceutical composition is as shown in the table below:

| Composition | |
|---|---|
| C2a | CXCL5; anti-CCL1; anti-IL1b; anti-M-CSF; anti-CCL24 |
| C3a | CCL8; CCL7; OPG; IL-10; anti-CCL24 |
| C4a | CCL8; CCL7; OPG; IL-10; CXCL5; anti-CCL1; anti-IL1b; anti-M-CSF |
| C5a | CCL20; CXCL6; OPG; IL-10; anti-IL1b; anti-M-CSF |
| C6a | CCL20; CXCL6; OPG; IL-10; CXCL5; anti-CCL1; anti-CCL24 |
| C7a | CCL20; CXCL6; CCL8; CCL7; anti-IL1b; anti-M-CSF; anti-CCL24 |
| C8a | CCL20; CXCL6; CCL8; CCL7; CXCL5; anti-CCL1 |
| C9a | PGE2; CXCL6; CCL7; IL-10; anti-CCL1; anti-M-CSF |
| C10a | PGE2; CXCL6; CCL7; IL-10; CXCL5; anti-IL1b; anti-CCL24 |
| C11a | PGE2; CXCL6; CCL8; OPG; anti-CCL1; anti-M-CSF; anti-CCL24 |
| C12a | PGE2; CXCL6; CCL8; OPG; CXCL5; anti-IL1b |
| C13a | PGE2; CCL20; CCL7; OPG; anti-CCL1; anti-IL1b |
| C14a | PGE2; CCL20; CCL7; OPG; CXCL5; anti-M-CSF; anti-CCL24 |
| C15a | PGE2; CCL20; CCL8; IL-10; anti-CCL1; anti-IL1b; anti-CCL24 |
| C16a | PGE2; CCL20; CCL8; IL-10; CXCL5; anti-M-CSF |
| C17a | CXCL5; CXCL6; anti-CCL1; CCL20 |
| C18a | IL-10; OPG; anti-CCL1; CCL20 |
| C19a | IL-10; OPG; CXCL5; CXCL6 |
| C20a | anti-CCL24; OPG; CXCL6; CCL20 |
| C21a | anti-CCL24; OPG; CXCL5; anti-CCL1 |
| C22a | anti-CCL24; IL-10; CXCL6; anti-CCL1 |
| C23a | anti-CCL24; IL-10; CXCL5; CCL20 |
| C24a | anti-CCL1 |
| C25a | anti-CCL24 |
| C26a | OPG |
| C27a | CXCL5 |
| C28a | anti-CCL1; anti-CCL24 |
| C29a | anti-CCL1; OPG |
| C30a | anti-CCL1; CXCL5 |
| C31a | anti-CCL24; OPG |
| C32a | anti-CCL24; CXCL5 |
| C33a | OPG; CXCL5 |
| C34a | anti-CCL1; anti-CCL24; OPG |
| C35a | anti-CCL1; anti-CCL24; CXCL5 |
| C36a | anti-CCL1; OPG; CXCL5 |
| C37a | anti-CCL24; OPG; CXCL5 |
| C38a | anti-CCL1; anti-CCL24; OPG; CXCL5 |

In another example, the present application discloses the method as described herein, wherein the pharmaceutical composition comprises CXCL5 and an anti-CCL24 antibody (C32a).

In yet another example, the present application discloses the method as described herein, wherein the immunological disorder is an alloimmune disease or an autoimmune disease.

In a further example, the present application disclose the method as described herein, wherein the alloimmune disease is selected from the group consisting of graft versus host disease (GVHD) after allogeneic hematopoietic cell transplantations, alloimmune disease resulting from skin transplant, alloimmune disease resulting from kidney transplant, alloimmune disease resulting from liver transplant, and hemolytic disease of the foetus and newborn.

In yet another example, the present application discloses the method as described herein, wherein the autoimmune disease is selected from the group consisting of systemic lupus erythematosus (SLE), lupus nephritis, type-I diabetes mellitus, systemic sclerosis, inflammatory bowel disease (IBD) and Crohn's disease.

In a further example, the present application discloses the method as disclosed herein, wherein the pharmaceutical composition results in a decrease in the concentration of one or more of the circulating pro-inflammatory cytokines selected from the group consisting of IFN-γ, IL-6, IL-17A, IL-8, MIP-1β and MCP-1 in the subject.

In one example, the present invention discloses the method as described herein, wherein the pharmaceutical composition results an increase or a decrease in the concentration of at least one mesenchymal stromal cell-derived protein in a subject results in an immunosuppressive effect, wherein the mesenchymal stromal cell-derived protein is selected from the group consisting of PGE2 (prostaglandin E2), OPG, CCL7, CCL8, CCL20, IL-10, CXCL5, CXCL6, M-CSF, IL-1β, CCL-1 and CCL24.

In a further aspect, the present invention refers to a kit comprising at least one antibody and at least one mesenchymal stromal cell-derived protein as defined herein.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
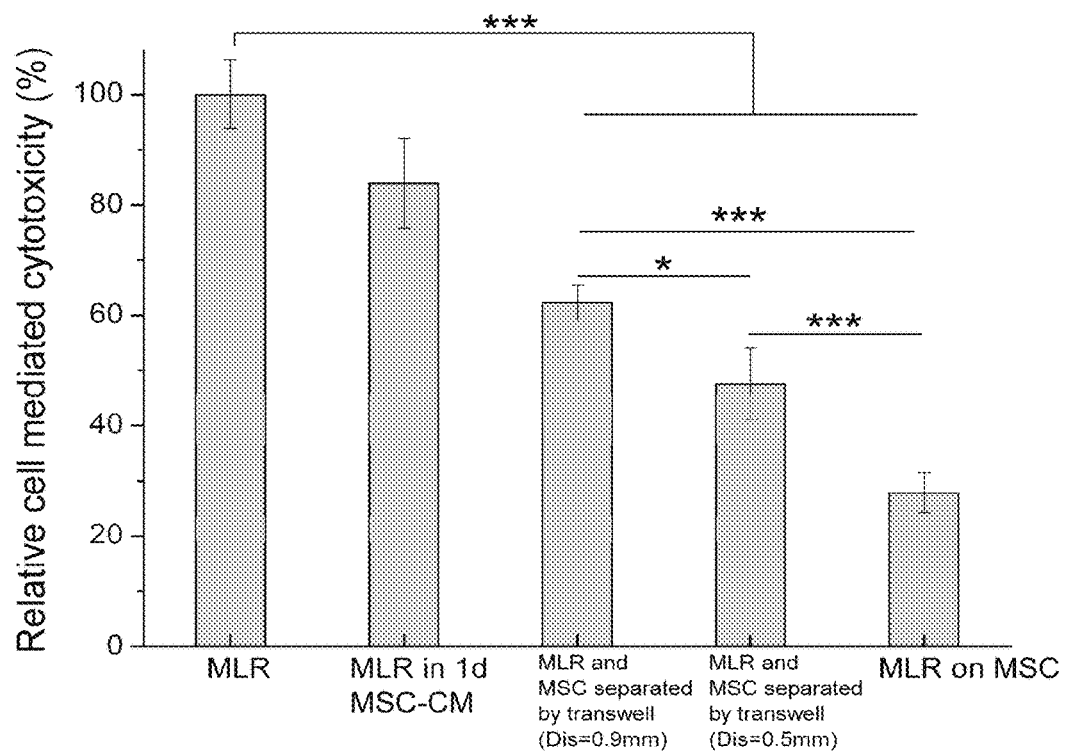
FIG. 1 shows a column graph with data indicating that the immunosuppressive effect of BM-MSC is mainly attributable to soluble factors. Mixed lymphocyte reaction (MLR) experiments were initiated with $1.6 \times 10^5$ of two HLA-mismatched UCB-MNCs at 15:1 E/T ratio for 20 hours. Cell mediated cytotoxicity was determined by LDH detection. Transwell inserts with a pore size of 8 μm were used. The different distance between insert and well bottom was varied. Results were expressed as mean±S.D. For multiple comparisons, Bonferroni's test was used to correct the p-value for t-test (*$p<0.05$; $p<0.01$; *$p<0.001$).

While shown to be effective in modulating or treating immunological disorders, mesenchymal stromal cell (also known as mesenchymal stem cell) therapies come with their own distinct set of unwanted side effects. Disclosed herein are methods and compositions for modulating immune responses, for example unforeseen long-term complications, potential tumorigenicity and uncontrolled differentiation to unwanted cells or tissues.

As used herein, the term "immunological disorder" refers to disorders pertaining to an abnormal reaction of the immune system. Immunological disorders can be classified into immunodeficiency, autoimmune disease and hypersensitivity. Thus, in one example, the immunological disorder is an alloimmune disease or an autoimmune disease.

As used herein, the terms "alloimmune" or "alloimmunity" refer to an immune response to non-self antigens from members of the same species, which are called alloantigens or isoantigens. Two major types of alloantigens are blood group antigens and histocompatibility antigens. In alloimmunity, the body creates antibodies against the alloantigens, attacking transfused blood, allotransplanted tissue, and even the fetus in some cases. Alloimmune (isoimmune) response results in graft rejection, which is manifested as deterioration or complete loss of graft function. In contrast, autoimmunity is an immune response to the self's own antigens. (The allo-prefix means "other", whereas the auto-prefix means "self".) Alloimmunization (isoimmunization) is the process of becoming alloimmune, that is, developing the relevant antibodies for the first time. Without being bound by theory, alloimmunity is thought to be caused by the difference between products of highly polymorphic genes, primarily genes of the major histocompatibility complex, of the donor and graft recipient. These products are recognized by T-lymphocytes and other mononuclear leukocytes which infiltrate the graft and damage it.

The terms "autoimmune" or "autoimmunity" refer to the scenario wherein the system of immune responses of an organism turns against its own healthy cells and tissues. Any disease that results from such an aberrant immune response is termed an autoimmune disease. Prominent examples include, but are not limited to, celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), and dermatomyositis (DM).

Autoimmune diseases, or immunological disorders in general, are often treated with steroids, among others. The intent is to suppress the aberrant immune response, commonly using immunosuppressants, to which steroid compounds below. The term "immune suppressive", "immunosuppressive" or "immunosuppression" refers to a reduction in the efficacy or the activation/initiation of the immune system. This may or may not influence the immune system's capability of fighting infections. Immunosuppression may result from certain diseases, such as AIDS or lymphoma, or can be induced or caused by using certain drugs, such as some of those used to treat cancer. Immunosuppression may also be deliberately induced with drugs, for example, in preparation for a bone marrow transplant or other organ transplantation, with the view of preventing the rejection of a transplant by the host. Immunosuppression can also be known as immunodepression.

Further examples of autoimmune diseases are, but are not limited to, myocarditis, post-myocardial infarction syndrome, post-pericardiotomy syndrome, sub-acute bacterial endocarditis (SBE), systemic lupus erythematosus (SLE), lupus nephritis, type-I diabetes mellitus, anti-glomerular basement membrane nephritis, interstitial cystitis, autoimmune hepatitis, primary biliary cirrhosis (PBC), primary sclerosing cholangitis, anti-synthetase syndrome, alopecia areata, autoimmune angioedema, autoimmune progesterone dermatitis, autoimmune urticarial, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen planus, lichen sclerosus, linear IgA disease (LAD), morphea, pemphigus vulgaris, pityriasis lichenoides et varioliformis acuta, Mucha-Habermann disease, psoriasis, systemic scleroderma, vitiligo, Addison's disease, autoimmune polyendocrine syndrome (APS) type 1, autoimmune polyendocrine syndrome (APS) type 2, autoimmune polyendocrine syndrome (APS) type 3, autoimmune pancreatitis (AIP), autoimmune thyroiditis, Ord's thyroiditis, Graves' disease, autoimmune oophoritis, endometriosis, autoimmune orchitis, Sjögren's syndrome, autoimmune enteropathy, coeliac disease, microscopic colitis, ulcerative colitis, antiphospholipid syndrome (APS, APLS), aplastic anemia, autoimmune hemolytic anemia, autoimmune lymphoproliferative syndrome, autoimmune neutropenia, autoimmune thrombocytopenic purpura, cold agglutinin disease, essential mixed cryoglobulinemia, evans syndrome, paroxysmal nocturnal hemoglobinuria, pernicious anemia, pure red cell aplasia, thrombocytopenia, adiposis dolorosa, adult-onset Still's disease, ankylosing Spondylitis, CREST syndrome, drug-induced lupus, enthesitis-related arthritis, eosinophilic fasciitis, Felty syndrome, IgG4-related disease, juvenile arthritis, Lyme disease (Chronic), mixed connective tissue disease (MCTD), palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, undifferentiated connective tissue disease (UCTD), dermatomyositis, fibromyalgia, inclusion body myositis, myositis, myasthenia gravis, neuromyotonia, paraneoplastic cerebellar degeneration, polymyositis, acute disseminated encephalomyelitis (ADEM), acute motor axonal neuropathy, anti-N-Methyl-D-Aspartate (Anti-NMDA) receptor encephalitis, balo concentric sclerosis, Bickerstaff's encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis (pattern II), Oshtoran Syndrome, pediatric Autoimmune Neuropsychiatric Disorder Associated with Streptococcus (PANDAS), progressive inflammatory neuropathy, Restless leg syndrome, Stiff person syndrome, Sydenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease (AIED), Ménière's disease, Behçet's disease, eosinophilic granulomatosis with polyangiitis (EGPA), giant cell arteritis, granulomatosis with polyangiitis (GPA), IgA vasculitis (IgAV), Kawasaki's disease, leukocytoclastic vasculitis, lupus vasculitis, rheumatoid vasculitis, microscopic polyangiitis (MPA), polyarteritis nodosa (PAN), polymyalgia rheumatic, urticarial vasculitis, vasculitis, primary immune deficiency and Crohn's disease.

In another example, the immunological disorder is, but is not limited to, myocarditis, post-myocardial infarction syndrome, post-pericardiotomy syndrome, sub-acute bacterial endocarditis (SBE), systemic lupus erythematosus (SLE), lupus nephritis, type-I diabetes mellitus and Crohn's disease.

Immunological disorders can also be classified by organs and or tissues that are affected by the disorder. For example, the organs and tissue types effected by immunological disorders are, but not limited to, major organs, such as heart, kidney, liver, lung, skin; glands, for example, endocrine, adrenal gland, multi-glandular, pancreas, thyroid gland; exocrine organs, such as reproductive organs, salivary glands; organs of the digestive system; various types of tissue, for example, blood, connective tissue, systemic tissue, and multi-organ tissue, muscle, nervous system, eyes, ears and vascular system.

The term "GVHD", also known as Graft-versus-host-disease, as used herein, refers to a medical complication that can occur after a stem cell or bone marrow transplant. With GVHD, the newly transplanted donor cells attack the transplant recipient's body. GVHD may occur after a bone marrow or stem cell transplant in which someone receives bone marrow tissue or cells from a donor. This type of transplant is called allogeneic. The new, transplanted cells regard the recipient's body as foreign. When this happens, the newly transplanted cells attack the recipient's body. GVHD does not occur when someone receives his or her own cells during a transplant. This type of transplant is called autologous. Before a transplant, tissue and cells from possible donors are checked to see how closely they match the person having the transplant. GVHD is less likely to occur, or symptoms will be milder, when the match is close. The chance of GVHD is around 30 to 40% when the donor and recipient are related and around 60 to 80% when the donor and recipient are not related. There are two types of GVHD: acute and chronic. Symptoms in both acute and chronic GVHD range from mild to severe. Acute GVHD usually happens within the first 6 months after a transplant, while chronic GVHD usually starts more than 3 months after a transplant, and can last a lifetime.

The term "SLE" refers to the disease "systemic lupus erythematosus", an autoimmune disease, whereby the cause is not fully known. In this disease, the body's immune system mistakenly attacks healthy tissue and can affect the skin, joints, kidneys, brain, and other organs. SLE may also be caused by certain drugs.

Without being bound by theory, it has been suggested that mesenchymal stromal cell (MSC; also known as mesenchymal stem cell) mediated immunosuppression works via paracrine signalling, which include a variety of soluble factors such as, for example, transforming growth factor-$\beta$ (TGF-$\beta$), IL-10, hepatocyte growth factor (HGF), indoleamine, dioxygenase (IDO), prostaglandins E2 (PGE2), Nitric oxide (NO), TNF-$\alpha$ stimulated gene/protein 6 (TSG-6), heme oxygenase-1 (HO), galectin-1 and HLA-Gs. Thus, it is shown in the present disclosure that it is possible to use soluble factors that influence paracrine signalling, as those present in the MSC secretome (that is, a cluster of effective soluble factors that is secreted by mesenchymal stromal cells) to emulate the effect of MSC therapy, or even to replace MSC therapy entirely.

As used herein, the term "MSC-derived" or "mesenchymal stromal cell-derived" refers to substances that are obtained or derived from a specific source. In the present disclosure, the term "mesenchymal stromal cell" is a multipotent stromal cell that can differentiate into a variety of cell types, including, but not limited to osteoblasts (bone cells), chondrocytes (cartilage cells), myocytes (muscle cells) and adipocytes (fat cells). These cells are also known as "mesenchymal stem cells" due to their multipotency. This biologically important cell population is able to support hematopoiesis, can differentiate along mesenchymal and non-mesenchymal lineages in vitro, is capable of suppressing alloresponses and appear to be non-immunogenic. These cells are known to either secrete certain proteins and/or compounds, which is turn influence the microenvironment around the cells, or when not directly expressing the proteins themselves, mesenchymal stromal cells are known to influence the downstream expression of other proteins, which for example, may be affected by the presence or absence of a mesenchymal stromal cell. That is to say that the presence of a mesenchymal stromal cell within the environment of another cell can cause the other cell to start producing, or even secreting, certain proteins. Therefore, disclosed herein are both compounds and/or proteins secreted by the mesenchymal stromal cells themselves and are therefore considered to be derived from MSCs as they are specifically obtained from MSCs, as well as proteins and compounds that are produced and/or secreted as a result of the presence of mesenchymal stromal cells within the cell environment. Included therein is also the downstream expression of proteins that is initiated via one or more expression cascades due to the presence of mesenchymal stromal cells in the microenvironment.

Thus, the present disclosure describes, in one example, a pharmaceutical composition comprising at least one antibody and at least one mesenchymal stromal cell-derived protein. In another example, the pharmaceutical composition comprises between 1 to 12 antibodies and proteins. In another example, the pharmaceutical composition comprises 1, 2, 3, or 4 antibodies and 1, 2, 3, 4, 5, 6, 7 or 8 proteins. In another example, the pharmaceutical composition comprises at least two antibodies and at least two proteins. In one example, the method of treatment as disclosed herein comprises the use of at least one antibody and/or at least one mesenchymal stromal cell-derived protein. In another example, the pharmaceutical composition as disclosed herein comprises at least one antibody and at least one mesenchymal stromal cell-derived protein, wherein the antibody targets one or more of the cytokines selected from the group consisting of macrophage colony-stimulating factor (M-CSF), Interleukin-1beta (IL-1$\beta$), CCL-1 (I-309) and CCL24 (Eotaxin-2); wherein the mesenchymal stromal cell-derived protein is selected from the group consisting of PGE2 (prostaglandin E2), OPG, CCL7 (MCP-2), CCL8 (MCP-3), CCL20 (MIP-3$\alpha$), CXCL5 (ENA-78), IL-10 and CXCL6 (GCP-2).

As used herein, the term "serial factorial designs" refers a type of statistical experiment design. There are two types of "factorial design". One is a "full factorial design", and another is a "fractional factorial design". In statistics, a full factorial design is an experiment whose design consists of two or more factors, each with discrete possible values or "levels", and whose experimental units take on all possible combinations of these levels across all such factors. Such an experiment allows the investigator to study the effect of each factor on the response variable, as well as the effects of interactions between factors on the response variable. If the number of combinations in a full factorial design is too high to be logistically feasible, a fractional factorial design may be done, in which some of the possible combinations (usually at least half) are omitted. In this present disclosure, two fractional and one full factorial designs were used, hence the term used herein to describe the analysis experiments performed is "serial factorial designs".

As disclosed herein, two mesenchymal stromal cell (MSC)-derived factors were identified that exhibited concerted immunomodulation effect in mixed lymphocyte reaction (MLR) through screening MSC paracrine secretome with factorial design (FD).

The term "mixed lymphocyte reaction (MLR)" refers to an ex vivo, cellular immune assay that occurs between two allogeneic lymphocyte populations (same species but genetically distinct). The assay set-up consists of purifying responder lymphocytes from peripheral blood, thymus, lymph nodes or spleen and co-culturing these with stimulator cells. Stimulator cell populations that also contain T-cells (also known as a two-way mixed lymphocyte reaction) will replicate in the presence of the responder cells, whereas in a one-way mixed lymphocyte reaction, stimulator cells are prevented from replicating by irradiation or treatment with, for example, mitomycin C or a DNA cross-linker to prevent cell replication. The MLR cell-based assay is used in research in order to test, measure and correlate in vitro T cell function and also to elucidate cellular immune function. Furthermore, MLR assays enable the characterization of the lymphocytes, accessory cells (for example, dendritic cells, macrophage and the like) and cytokines that participate in the MLR reactions.

As shown herein, in order to avoid above-mentioned complications, it is intended to replicate and substitute MSC immune-regulatory therapy by its secretome. Ten MSC-derived potential soluble factors accountable for the immunosuppression were shortlisted by cytokine antibody array screening. Six of them (MIP-3α (CCL20), MCP-3 (CCL8), ENA-78 (CXCL5), OPG, GCP-2 (CXCL6), MCP-2 (CCL7)) were upregulated and four of them (M-CSF, IL-1β, I-309 (CCL1), and Eotaxin-2 (CCL24)) were downregulated.

In one example, the antibody results in a decrease in concentration of the target cytokine. In one example, the target cytokine is, but is not limited to, one or more of the following: M-CSF, IL-1β, I-309 (CCL1), Eotaxin-2 (CCL24). In another example, the mesenchymal stromal cell-derived protein results in an increase of PGE2, IL-10, OPG, CCL7 (MCP-2), CCL8 (MCP-3), CCL20 (MIP-3α), CXCL5 (ENA-78) or CXCL6 (GCP-2). In yet another example, the antibody results in a decrease in concentration of the target cytokine; and the mesenchymal stromal cell-derived protein results in an increase of PGE2, IL-10, OPG, CCL7 (MCP-2), CCL8 (MCP-3), CCL20 (MIP-3α), CXCL5 (ENA-78) or CXCL6 (GCP-2). In another example, the pharmaceutical composition as disclosed herein results an increase or a decrease in the concentration of at least one mesenchymal stromal cell-derived protein in a subject results in an immunosuppressive effect, wherein the mesenchymal stromal cell-derived protein is selected from the group consisting of PGE2 (prostaglandin E2), OPG, CCL7, CCL8, IL-10, CCL20, CXCL5, CXCL6, M-CSF, IL-1β, CCL-1 and CCL24.

In order to attain the desired effect disclosed in the present application, in one example, the antibody targets one or more of the cytokines. In another example, the one or more cytokines is, but are not limited to, macrophage colony-stimulating factor (M-CSF), Interleukin-1beta (IL-1β), CCL-1 (I-309) and CCL24 (Eotaxin-2).

In one example, the proteins are mesenchymal stromal cell-derived protein. In another example, the mesenchymal stromal cell-derived protein is, but is not limited to, PGE2 (prostaglandin E2), OPG, CCL7 (MCP-2), CCL8 (MCP-3), CCL20 (MIP-3α), CXCL5 (ENA-78), IL-10 and CXCL6 (GCP-2).

As used herein, the terms "increase" and "decrease" refer to the relative alteration of a chosen target or characteristic in a subset of a population (for example a diseased cell) in comparison to the same target or characteristic as present in a control population (for example, a disease free cell) or compared to the whole population. An increase indicates a change on a positive scale, whereas a decrease indicates a change on a negative scale. The term "change", as used herein, also refers to the difference between a chosen target or characteristic of an isolated population subset (for example samples obtained from diseased patients) in comparison to the same trait or characteristic in a control population (for example, samples from disease-free subjects) or in the population as a whole. However, this term is without valuation of the difference seen. Where applicable, the terms "increase" and "decrease" may be replaced with the terms "upregulated" and "downregulated", for example when referring to a change in the expression profile of, for example, genes and proteins.

Inhibiting any of these downregulated proteins or promoting any of these upregulated proteins could not fully mimic the immunosuppressive capability of MSC, suggested that MSC modulated immune reaction through an interacting network of factors. Through serial factorial designs (FD), a two factor (2F)-cocktail comprising CXCL5 and anti-CCL24 antibody was finally established. It exhibited concerted immunomodulation effect in MLR-an in vitro GVHD model. It also showed excellent in vivo immunosuppressive effect in term of ameliorating GVHD and SLE symptoms and improving survival. This identified 2F cocktail could be a potential chemically defined substitute for MSC in immunological disorders therapy.

Thus, in a first aspect the present invention refers to a pharmaceutical composition comprising at least one antibody and at least one mesenchymal stromal cell-derived protein, wherein the antibody targets one or more of the cytokines, wherein the cytokine is, but is not limited to macrophage colony-stimulating factor (M-CSF), Interleukin-1beta (IL-1β), CCL-1 (I-309) and CCL24 (Eotaxin-2); wherein the mesenchymal stromal cell-derived protein is, but is not limited to, PGE2 (prostaglandin E2), IL-10, OPG, CCL7 (MCP-2), CCL8 (MCP-3), CCL20 (MIP-3α), CXCL5 (ENA-78) and CXCL6 (GCP-2).

In one example, one or more antibodies are either anti-CCL1, or anti CCL24, or both, while the one or more mesenchymal stromal cell-derived protein is as defined herein. In another example, one or more antibodies are as disclosed herein, while the one or more mesenchymal stromal cell-derived proteins are, but are not limited to, CXCL5 and OPG. In one example, one or more antibodies are either anti-CCL1, or anti CCL24, or both, while the one or more mesenchymal stromal cell-derived protein is either OPG, or CXCL5 , or both. In one example, the antibody is anti-CCL1 in a concentration of 2 μg/ml, and the one or more mesenchymal stromal cell-derived protein is either OPG, or CXCL5 or both. In another example, the antibody is anti-CCL24 in a concentration of 2 μg/ml, and the one or more mesenchymal stromal cell-derived protein is either OPG, or CXCL5 or both. In another example, the antibody is anti-CCL24 and anti-CCL1, both each in a concentration of 2 μg/ml, and the one or more mesenchymal stromal cell-derived protein is either OPG, or CXCL5 or both. In one example, the one or more antibody is anti-CCL1, or anti-CCL24, or both, and the mesenchymal stromal cell-derived protein is OPG in a concentration of 10 ng/ml. In one example, the one or more antibody is anti-CCL1, or anti-CCL24, or both, and the mesenchymal stromal cell-derived protein is CXCL5 in a concentration of 50 ng/ml. In yet one example, the one or more antibody is anti-CCL1, or anti-CCL24, or both, and the mesenchymal stromal cell-derived protein is OPG in a concentration of 10 ng/ml and CXCL5 in a concentration of 50 ng/ml.

In one example, the pharmaceutical composition can comprise the components as provided in Table 1 below, wherein, in on example, the pharmaceutical composition is any composition except for C24a to C27a. In another example, the method is as disclosed herein, wherein the pharmaceutical composition is as shown in Table 1 below.

TABLE 1

List of various compositions

| Composition | |
|---|---|
| C2a | CXCL5; anti-CCL1; anti-IL1b; anti-M-CSF; anti-CCL24 |
| C3a | CCL8; CCL7; OPG; IL-10; anti-CCL24 |
| C4a | CCL8; CCL7; OPG; IL-10; CXCL5; anti-CCL1; anti-IL1b; anti-M-CSF |
| C5a | CCL20; CXCL6; OPG; IL-10; anti-IL1b; anti-M-CSF |
| C6a | CCL20; CXCL6; OPG; IL-10; CXCL5; anti-CCL1; anti-CCL24 |
| C7a | CCL20; CXCL6; CCL8; CCL7; anti-IL1b; anti-M-CSF; anti-CCL24 |
| C8a | CCL20; CXCL6; CCL8; CCL7; CXCL5; anti-CCL1 |
| C9a | PGE2; CXCL6; CCL7; IL-10; anti-CCL1; anti-M-CSF |
| C10a | PGE2; CXCL6; CCL7; IL-10; CXCL5; anti-IL1b; anti-CCL24 |
| C11a | PGE2; CXCL6; CCL8; OPG; anti-CCL1; anti-M-CSF; anti-CCL24 |
| C12a | PGE2; CXCL6; CCL8; OPG; CXCL5; anti-IL1b |
| C13a | PGE2; CCL20; CCL7; OPG; anti-CCL1; anti-IL1b |
| C14a | PGE2; CCL20; CCL7; OPG; CXCL5; anti-M-CSF; anti-CCL24 |
| C15a | PGE2; CCL20; CCL8; IL-10; anti-CCL1; anti-IL1b; anti-CCL24 |
| C16a | PGE2; CCL20; CCL8; IL-10; CXCL5; anti-M-CSF |
| C17a | CXCL5; CXCL6; anti-CCL1; CCL20 |
| C18a | IL-10; OPG; anti-CCL1; CCL20 |
| C19a | IL-10; OPG; CXCL5; CXCL6 |
| C20a | anti-CCL24; OPG; CXCL6; CCL20 |
| C21a | anti-CCL24; OPG; CXCL5; anti-CCL1 |
| C22a | anti-CCL24; IL-10; CXCL6; anti-CCL1 |
| C23a | anti-CCL24; IL-10; CXCL5; CCL20 |
| C24a | anti-CCL1 |
| C25a | anti-CCL24 |
| C26a | OPG |
| C27a | CXCL5 |
| C28a | anti-CCL1; anti-CCL24 |
| C29a | anti-CCL1; OPG |
| C30a | anti-CCL1; CXCL5 |
| C31a | anti-CCL24; OPG |
| C32a | anti-CCL24; CXCL5 |
| C33a | OPG; CXCL5 |
| C34a | anti-CCL1; anti-CCL24; OPG |
| C35a | anti-CCL1; anti-CCL24; CXCL5 |
| C36a | anti-CCL1; OPG; CXCL5 |
| C37a | anti-CCL24; OPG; CXCL5 |
| C38a | anti-CCL1; anti-CCL24; OPG; CXCL5 |

In one example, the pharmaceutical composition comprises CXCL5 and an anti-CCL24 antibody (C32a).

Therefore, in one example, the pharmaceutical composition is according to any one of C2 to C16 as shown in Table 3. In one example, the pharmaceutical composition comprises CXCL5, anti-CCL1, anti-IL-1β, anti M-CSF and anti-CCL24 (C2a). In another example, the pharmaceutical composition comprises CCL8, CCL7, OPG, IL-10 and anti-CCL24 (C3a). In another example, the pharmaceutical composition comprises CCL8, CCL7, OPG, IL-10, CXCL5, anti-CCL1, anti-IL-1β, and anti M-CSF (C4a). In another example, the pharmaceutical composition comprises CCL20, CCL6, OPG, IL-10, anti-IL-1β and anti-M-CSF (C5a). In another example, the pharmaceutical composition comprises CCL20, CXCL6, OPG, IL-10, CXCL5, anti-CCL1, and anti-CCL24 (C6a). In another example, the pharmaceutical composition comprises CCL20, CXCL6, CCL8, CCL7, anti-IL-1β, anti-M-CSF, and anti-CCL24 (C7a). In another example, the pharmaceutical composition comprises CCL20, CXCL6, CCL8, CCL7, CXCL5, and anti-CCL1 (C8a). In another example, the pharmaceutical composition comprises PGE2, CXCL6, CCL7, IL-10, anti-CCL1, and anti-M-CSF (C9a). In another example, the pharmaceutical composition comprises PGE2, CXCL6, CCL7, IL-10, CXCL5, anti-IL-1β, and anti-CCL24 (C10a). In another example, the pharmaceutical composition comprises PGE2, CXCL6, CCL8, OPG, anti-CCL1, anti-M-CSF, and anti-CCL24 (C11a). In another example, the pharmaceutical composition comprises PGE2, CXCL6, CCL8, OPG, CXCL5, and anti-IL-1β (C12a). In another example, the pharmaceutical composition comprises PGE2, CCL20, CCL7, OPG, anti-CCL1, and anti-IL-1β (C13a). In another example, the pharmaceutical composition comprises PGE2, CCL20, CCL7, OPG, CXCL5, and anti-M-CSF and anti-CCL24 (C14a). In another example, the pharmaceutical composition comprises PGE2, CCL20, CCL8, IL-10, anti-CCL1, anti-IL-1β and anti-CCL24 (C15a). In another example, the pharmaceutical composition comprises PGE2, CCL20, CCL8, IL-10, CXCL5 and anti-M-CSF (C16a).

In a further example, the pharmaceutical composition is according to any one of C17 to C23 as shown in Table 4. In one example, the pharmaceutical composition comprises CXCL5, CXCL6, anti-CCL1, and CCL20 (C17a). In another example, the pharmaceutical composition comprises IL-10, OPG, anti-CCL1, and CCL20 (C18a). In one example, the pharmaceutical composition comprises CXCL5, CXCL6, IL-10, and OPG (C19a). In one example, the pharmaceutical composition comprises anti-CCL24, CXCL6, OPG, and CCL20 (C20a). In one example, the pharmaceutical composition comprises anti-CCL24, CXCL5, OPG, and anti-CCL1 (C21a). In one example, the pharmaceutical composition comprises anti-CCL24, CXCL6, IL-10, and CCL1 (C22a). In one example, the pharmaceutical composition comprises anti-CCL24, CXCL5, IL-10, and CCL20 (C23a).

In another example, the pharmaceutical composition is according to any one of C24 to C38 as shown in Table 5. In another example, the pharmaceutical composition comprises anti-CCL24 and anti-CCL1 (C28a). In another example, the pharmaceutical composition comprises OPG and anti-CCL1 (C29a). In another example, the pharmaceutical composition comprises CXCL5 and anti-CCL1 (C30a). In another example, the pharmaceutical composition comprises anti-CCL24 and OPG (C31a). In another example, the pharmaceutical composition comprises anti-CCL24 and CXCL5 (C32a). In another example, the pharmaceutical composition comprises OPG and CXCL5 (C33a). In another example, the pharmaceutical composition comprises anti-CCL24, anti-CCL1 and OPG (C34a). In another example, the pharmaceutical composition comprises anti-CCL24, anti-CCL1, and CXCL5 (C35a). In another example, the pharmaceutical composition comprises OPG, CXCL5 and anti-CCL1 (C36a). In another example, the pharmaceutical composition comprises anti-CCL24 OPG and CXCL5 (C37a). In another example, the pharmaceutical composition comprises anti-CCL24, anti-CCL1, OPG and CXCL5 (C38a). In another example, the pharmaceutical composition comprises PGE2, CCL20, CXCL6, CCL8, CCL7, OPG, IL-10, CXCL5, anti-CCL1, anti-IL1 b, anti-M-CSF and anti-CCL24 (full panel as shown in Table 3).

As a person skilled in the art would appreciate, the concentrations of the individual components disclosed herein are to be present in a concentration capable of or resulting in the desired effect, which is the modulation of the host immune system.

Thus, in one example, the pharmaceutical composition is as disclosed herein, wherein the antibody is present in a concentration of about 0.05 µg to 5 µg, 0.05 µg to 0.7 µg, 0.5 µg/ml to about 5 µg/ml, about 1 µg/ml to about 2 µg/ml, about 2 µg/ml to about 3.5 µg/ml, about 4 µg/ml to about 5 µg/ml, about 3 µg/ml to about 4.5 µg/ml, about 0.05 µg, about 0.1 µg, about 0.25 µg, about 0.5 µg/ml, about 0.75 µg/ml, about 1 µg/ml, about 1.25 µg/ml, about 1.5 µg/ml, about 2.25 µg/ml, about 2.5 µg/ml, about 2.75 µg/ml, about 3.75 µg/ml, or about 4.8 µg/ml. In one example, the antibody is present in a concentration of about 1 µg/ml or about 2 µg/ml. The concentration of each antibody in a pharmaceutical composition is selected independently from all other components of the pharmaceutical composition. In one example, the concentration of anti-IL-1β, anti-M-CSF, independently, is less than 3 µg/ml, less than 2 µg/ml, or less than 1.5 µg/ml. In another example, the concentration of anti-CCL1 and anti-CCL24, independently, is less than 6 µg/ml, less than 5 µg/ml or less than 2.5 µg/ml.

Figure 3:
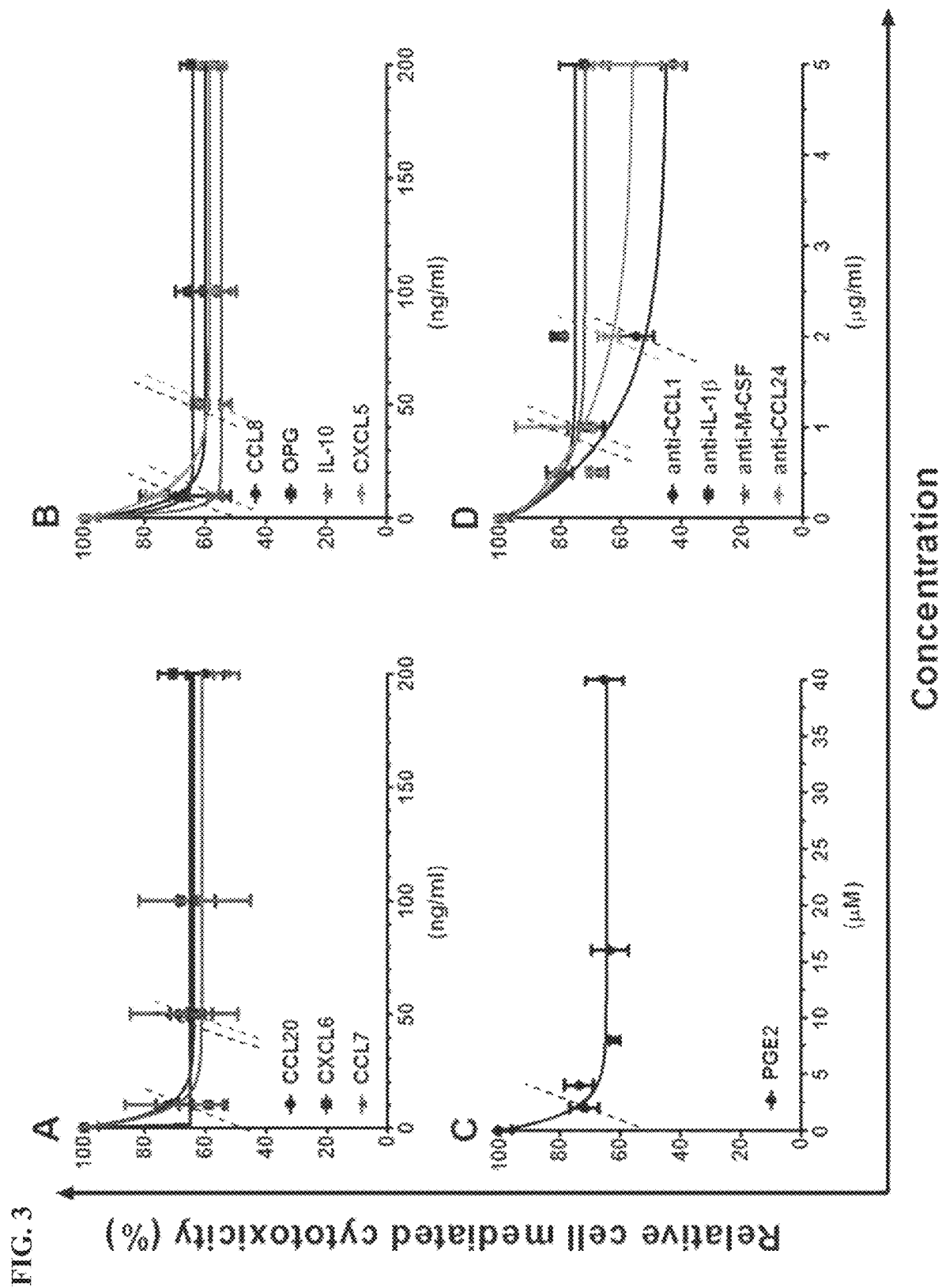
FIG. 3 shows dose response curves showing the determination of the optimal working concentration of each factor. (A-C) Dose response curves of upregulated factors. (D) Dose response curves of antibodies against downregulated factors. The titration was carried out on MLR system with 15:1 E/T ratio for 20 hours. Cell mediated cytotoxicity was determined by LDH detection. Results were expressed as mean±S.D.

In one example, the pharmaceutical composition is as disclosed herein, wherein the mesenchymal stromal cell-derived protein is present in a concentration of about 0.5 ng/mg to about 75 ng/ml, about 0.5 to about 10 ng/ml, about 0.5 to about 1 ng/ml, about 0.75 to about 5 ng/ml, 5 ng/ml to about 75 ng/ml, about 10 ng/ml to about 50 ng/ml, about 20 ng/ml to about 40 ng/ml, about 30 ng/ml to about 65 ng/ml, about 40 ng/ml to about 55 ng/ml, about 0.5 ng/ml, about 1 ng/ml, about 5 ng/ml, about 8 ng/ml, about 9 ng/ml, about 10 ng/ml, about 15 ng/ml, about 25 ng/ml, about 34 ng/ml, about 40 ng/ml, about 45 ng/ml, about 50 ng/ml, about 55 ng/ml, about 58 ng/ml, about 65 ng/ml, or about 70 ng/ml. In another example, the mesenchymal stromal cell-derived protein is present in a concentration of about 10 ng/ml or 50 ng/ml. The concentration of each mesenchymal stromal cell-derived protein in a pharmaceutical composition is selected independently from all other components of the pharmaceutical composition. In one example, the concentration of each of CCL20, CCL8, CCL7, CXCL6, CXCL5, OPG and IL-10, independently, is less than 60 ng/ml, less than 50 ng/ml, or less than 30 ng/ml. As shown in FIG. 3, the immunosuppressive effect of individual proteins would reach a plateau in the event that more than 50 ng/ml of protein is added during experimental analysis.

In one example, the pharmaceutical composition comprises CXCL6, OPG and IL-10 in a concentration of between about 5 µg/ml and about 15 µg/ml, CXCL5 and CCL20 in a concentration of between about 45 µg/ml and 55 µg/ml, and anti-CCL1 and anti-CCL24 in a concentration of between about 1 µg/ml and 2.5 µg/ml. In another example, the pharmaceutical composition comprises CXCL6, OPG and IL-10 in a concentration of about 10 µg/ml, CXCL5 and CCL20 in a concentration of about 50 µg/ml, and anti-CCL1 and anti-CCL24 in a concentration of about 2 µg/ml (C6; also termed 7F). In one example, the pharmaceutical composition comprises anti-CCL24 and anti-CCL1 in a concentration of between about 1 to 2.5 µg/ml, CXCL5 at a concentration of between about 45 µg/ml to 55 µg/ml, and OPG at a concentration of between about 5 µg/ml to 15 µg/ml. In another example, the pharmaceutical composition comprises anti-CCL24 and anti-CCL1 in a concentration of about 2 µg/ml, CXCL5 at a concentration of about 50 µg/ml, and OPG at a concentration of between about 10 µg/ml (C21). In one example, the pharmaceutical composition comprises anti-CCL24 in a range of 1 to 2.5 µg/ml and CXCL5 in a range of 40 to 60 ng/ml. In another example, the pharmaceutical composition comprises anti-CCL24 at a concentration of 2 µg/ml and CXCL5 in a concentration of 50 ng/ml (C32).

Also disclosed herein is a method of treating an immunological disorder. In one example, the method of treating an immunological disorder comprises administration of a pharmaceutical composition comprising at least one antibody and/or at least one mesenchymal stromal cell-derived protein, wherein the antibody targets one or more of the cytokines selected from the group consisting of macrophage colony-stimulating factor (M-CSF), Interleukin-1beta (IL-1β), CCL-1 (I-309) and CCL24 (Eotaxin-2); wherein the mesenchymal stromal cell-derived protein is selected from the group consisting of PGE2 (prostaglandin E2), OPG, CCL7 (MCP-2), CCL8 (MCP-3), CCL20 (MIP-3a), CXCL5 (ENA-78), IL-10 and CXCL6 (GCP-2). Thus, in one example, the immunological disorder is an alloimmune disease or an autoimmune disease. In one example, the alloimmune disease is selected from the group consisting of graft versus host disease (GVHD) after allogeneic hematopoietic cell transplantations, alloimmune disease resulting from skin transplant, alloimmune disease resulting from kidney transplant, alloimmune disease resulting from liver transplant, and hemolytic disease of the foetus and newborn. In another example, the autoimmune disease is selected from the group consisting of systemic lupus erythematosus (SLE), lupus nephritis, type-I diabetes mellitus, and Crohn's disease.

In one example, the method comprises administration of the pharmaceutical composition as defined herein. In another example, disclosed herein is a method of modulating the immune system, the method comprising administration of a pharmaceutical composition as defined herein. In another example, the method is as disclosed herein, wherein the pharmaceutical composition results an increase or a decrease in the concentration of at least one mesenchymal stromal cell-derived protein in a subject results in an immunosuppressive effect, wherein the mesenchymal stromal cell-derived protein is, but is not limited to, PGE2 (prostaglandin E2), OPG, CCL7, CCL8, CCL20, CXCL5, CXCL6, M-CSF, IL-1β, CCL-1 and CCL24. In another example, the method is as disclosed herein, wherein the pharmaceutical composition results in a decrease in the concentration of one or more of the circulating pro-inflammatory cytokines, whereby the cytokines are, but are not limited to IFN-γ, IL-6, IL-17A, IL-8, MIP-1β and MCP-1 in the subject. In one example, the method comprises administration of the pharmaceutical composition comprising CXCL5 and an anti-CCL24 antibody (C32a).

In one example, the method is as disclosed herein, wherein the pharmaceutical composition is according to any one of C2 to C16 as shown in Table 3. In another example, the method is as disclosed herein, wherein the pharmaceutical composition is according to any one of C17 to C23 as shown in Table 4. In yet another example, the method is as disclosed herein, wherein the pharmaceutical composition is according to any one of C24 to C38 as shown in Table 5. In a further example, the method is as disclosed herein, wherein the pharmaceutical composition comprises CXCL5 and an anti-CCL24 antibody (for example, C32 in Table 5 or C32a in Table 1).

The identified 2 factor "2F" cocktail, comprising CXCL5 and anti-CCL24 antibody, also showed in vivo immunosuppressive effect in ameliorating GVHD and systemic lupus erythematosus (SLE) symptoms and improving survival. In GVHD, it is shown to reduce cytotoxic T lymphocytes (CTLs), Th1 cells, Th17 cells, natural killer (NK) cells in the circulation and macrophages in the spleen, but not to affect human hematopoietic stem cells (HSCs) reconstitution in the bone marrow. Concurrently, it is shown to reduce pro-inflammatory cytokine IFN-γ, IL-6, IL-17A, IL-8, MIP-1β and MCP-1 in the circulation. In SLE, it is shown to reduce helper T cells, dendritic cells (DCs), monocytes and/or macrophages and natural killer cells (NK cells). Without being bound by theory, these results indicated the 2F cocktail mimics the immunomodulatory effect of MSCs by suppressing the proliferation and differentiation of multiple effector cells and reducing the secretion of a cluster of pro-inflammatory cytokines.

Thus, in one example, the pharmaceutical composition is as disclosed herein, wherein the pharmaceutical composition results in a reduction in the presence of at least one cell type, but not limited to, circulating cytotoxic T lymphocytes (CTLs), T helper 1 (Th1) cells, T helper 17 (Th17) cells, and natural killer (NK) cells of a subject, as well as splenic macrophages and NK cells of a subject in GVHD; helper T cells, DCs, monocytes/macrophages and NK cells of a subject in SLE.

ENA-78 (epithelial-derived neutrophil-activating protein 78, also called CXCL5) is a member of the CXC chemokines and acts as a potent chemo-attractant and activator of neutrophils through CXCR2 receptor. Neutrophils are traditionally considered, to be short-lived (6-8 h), terminally differentiated cells that do not recirculate. The potential existence of distinct neutrophil subsets with functional and phenotypic heterogeneity has not been widely considered or explored. However, more and more evidence is now challenging this scenario, and there is significant evidence for the existence of different neutrophil subsets under both physiological and pathological conditions. In severe systemic inflammation elicited by trauma or sepsis, neutrophils play a critical role. They contribute to collateral tissue damage during the initial inflammatory stage of sepsis. However, most deaths occur during the later compensatory anti-inflammatory response stage of the disease, when patients develop immunosuppression and succumb to additional infections. The latter indicates that despite notable neutrophilia, the host is immunocompromised and more prone to infections, suggesting alterations in the effector functions of neutrophils. Within this, it was revealed that systemic LPS leads to the presence of a previously undescribed neutrophil subset characterized by a distinct $CD16^{bright}CD62L^{dim}$ phenotype that was also detected in patients who had suffered severe injury. This neutrophil subset exhibited hypersegmented nuclear morphology, increased capability to produce ROS and suppressive T-cell proliferation via expression of Mac-1 and locally released ROS-dependent inhibition of T cell proliferation.

Eotaxin-2 (eosinophil chemotactic protein-2, also called CCL24) is small cytokine belonging to the CC chemokine family. CCL24 interacts with chemokine receptor CCR3 and exerts its activity on eosinophils, resting T cells and basophils. Eotaxins have been well documented its role in allergic conditions (such as asthma and rhinitis) and other inflammatory disorders characterized by eosinophils accumulation (inflammatory bowel disease, atopic dermatitis and dermatitis herpetiformis) through the release of reactive oxygen species (ROS) and induction of histamine and LTC-4 degranulation in basophils. It has been proposed as a therapeutic target for these conditions using antibodies against eotaxins or interfering eotaxin receptor with modified chemokines, small molecules specific antagonists for CCR3 and anti-CCR3 antibodies.

Without being bound by theory, based on the biological property of these two chemokines, it is possible to understand the immunosuppressive capacity of anti-CCL24 antibody. Anti-CCL24 antibody is shown to inhibit the proliferation of T cells, especially with regard to cytotoxic T lymphocytes (CTLs), Th1 and Th17 cells. The reduction of these three cell populations results in a reduction of IFN-γ secretion. Thus the proliferation of natural killer (NK) cells and macrophages is further reduced in a cascading manner.

All these repressed effector cells contribute to the immunosuppression. However, the immunosuppressive effect of chemokine CXCL5 found in the present application appears to run against to the general understanding of what CXCL5 does. Normally, CXCL5 is a neutrophil chemoattractant and will recruit more neutrophils if its concentration is increased. However, as shown herein, CXCL5 suppresses the proliferation of multiple effector cells, and reduces the pro-inflammatory cytokine secretion. Without being bound by theory, it is thought that CXCL5 exerts its immunosuppressive function through three possible mechanisms: (1) instantaneously increased CXCL5 concentration in blood by intravenous injection may reverse the chemokine gradient between the blood (high) and inflammatory tissues (low). This helps to recruit the infiltrated neutrophils and macrophages back from the inflammatory tissues to blood and release the inflammation burden in the tissues. This concept has been corroborated by the less lymphocyte infiltration in skin, intestine and kidney of GVHD mice as shown herein. (2) CXCL5 may help to promote the proliferation of immunosuppressive neutrophils. This neutrophil subset is characterized by a distinct $CD16^{bright}CD62L^{dim}$ phenotype and has demonstrated immunosuppression capacity in patients who have suffered severe injury. This neutrophil subset exhibits hypersegmented nuclear morphology, increased capability to produce ROS and suppressive T-cell proliferation via expression of Mac-1 and locally released ROS-dependent inhibition of T cell proliferation. In the xenograft GVHD model shown herein, there were no viable granulocytes in the cryopreserved PBMCs after two rounds of freeze/thaw processing. Hence, in the short run GVHD mice model, there were no human neutrophils, eosinophils and basophils engrafted due to the limitation of the animal model per se. However, a distinct mouse immunosuppressive neutrophil ($Ly6G^+CD11b^+$) population was observed when mice were treated with the 2FC (data not shown). This highly promoted mouse immunosuppressive neutrophils might also assist to ameliorate GVHD symptoms and improve mice survival. (3) CXCL5 concerts anti-CCL24 to suppress immune reaction through other immune cell types. In the in vitro screening model, the MLR was set up with two HLA-mismatched mononuclear cells, in which the granulocytes were removed by Ficoll-paque isolation. CXCL5 was still screened out as the key immunomediator even though there are no neutrophils involved in the reaction. Without being bound by theory, this result suggests that CXCL5 exerts its immunosuppressive function through other immune cell types.

The present disclosed also describes a kit comprising at least one antibody and at least one mesenchymal stromal cell-derived protein as defined herein.

The peptide, the antibody or the pharmaceutical composition as described herein and above can be formulated into compositions suitable for administration. Where applicable, a peptide and/or an antibody may be administered with a pharmaceutically acceptable carrier. A "carrier" can include any pharmaceutically acceptable carrier as long as the carrier can is compatible with other ingredients of the formulation and not injurious to the patient. Accordingly, pharmaceutical compositions for use may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Thus, in one example, the present disclosure described a pharmaceutical composition comprising, but not limited to, at least one peptide as described herein and at least one antibody as described herein. In one example, the pharmaceutical composition comprises a peptide as described herein. In another example, the pharmaceutical composition comprises an antibody as described herein. In yet another example, the pharmaceutical composition further comprises one or more pharmaceutically acceptable excipients, vehicles or carriers. Therefore, in one example, the peptide as disclosed herein may further comprise a compound selected from, but not limited to, a pharmaceutically acceptable carrier, a liposomal carrier, an excipient, an adjuvant or combinations thereof.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients. In one example, the pharmaceutical composition described herein is formulated for parenteral administration. In another example, the pharmaceutical composition described herein is formulated for intravenous administration. In another example, the pharmaceutical composition is formulated as admixture, whereby, for example, each compound is provided separately, to be mixed shortly before administration.

Compositions as described herein include, but are not limited to, solutions, emulsions, and liposome-containing formulations. These compositions may be generated from a variety of components that include, but are not limited to, preformed liquids, self-emulsifying solids and self-emulsifying semisolids.

The formulations as described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The composition, shape, and type of dosage forms of the pharmaceutical composition as disclosed herein will typically vary depending on the intended use. For example, a dosage form used in the acute treatment of a disease or a related disease may contain larger amounts of one or more of the active compound it comprises than a dosage form used in the chronic treatment of the same disease. Similarly, a parenteral dosage form may contain smaller amounts of one or more of the active compound it comprises than an oral dosage form used to treat the same disease or disorder. These and other ways in which specific dosage forms encompassed by this invention will vary from one another will be readily apparent to those skilled in the art. Examples of dosage forms include, but are not limited to: tablets; caplets; capsules, such as soft elastic gelatine capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms particularly suitable for parenteral administration to a patient; and sterile solids (e.g., crystalline or amorphous solids) that can be reconstituted to provide liquid dosage forms suitable for parenteral administration to a patient. Thus, in one example, the pharmaceutical composition as disclosed herein is provided in a form selected from, but not limited to, tablets, caplets, capsules, hard capsules, soft capsules, soft elastic gelatine capsules, hard gelatine capsules, cachets, troches, lozenges, dispersions, suppositories, ointments, cataplasms, poultices, pastes, powders, dressings, creams, plasters, solutions, injectable solutions, patches, aerosols, nasal sprays, inhalers, gels, suspensions, aqueous liquid suspensions, non-aqueous liquid suspensions, oil-in-water emulsions, a water-in-oil liquid emulsions, solutions, sterile solids, crystalline solids, amorphous solids, solids for reconstitution or combinations thereof.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation, or metabolites thereof, in the body of the patient. The administering physician can easily determine optimum dosages, dosing methodologies and repetition rates. Optimum dosages may vary depending on the relative potency of the composition, and can generally be estimated based on arithmetic means, for example based on $EC_{50}$ values found to be effective in in vitro and in vivo animal models, or based on the examples described herein. In general, dosage of the pharmaceutical composition according to the present disclosure is from about 0.01 µg to 100 g/kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the composition is administered in maintenance doses, ranging from 0.01 µg to 100 g/kg of body weight, once or more daily, to once every 2 years.

As mentioned above, a person skilled in the art would be able to ascertain, based on, for example, disease severity, the required dosage amount and dosage regime required to attain the desired clinical effect. The following is used as an illustrative example of an intravenous injection, which may be amended as required for other modes of administration. In one example, the method, as disclosed herein, is to be administered to a subject as at least one injection. In one example, more than a single injection may be administered to a patient at any given time. In yet another example, the method as disclosed herein may require that a single injection be administered to the patient more than once within a specified treatment timeframe or regime. In yet another example, the method as disclosed herein may require that more than two or more injections be administered to the patient more than once within a specified treatment timeframe or regime. This means, at according to clinical requirements, the subject may be given an initial treatment in the form of an injection, whereby further treatment may follow at interval of, for example, 3 day, 7 days, weekly, 2 weeks, fortnightly, 1 month, monthly, quarterly, biannually, annually or longer, depending on the treatment designed for the subject. If required, the method disclosed herein may also be used as in combination therapy with other drugs or pharmaceutical compositions.

It is also of note that efficacy of, for example, a single factor treatment, is dependent on the severity of the disease to be treated at the time of treatment onset. For example, based on the clinically known severity score for, for example, GVHD, it was found that the efficacy of the treatment of GVHD with for example, anti-CCL24, was dependent on the severity of the GVHD to be treated. That is to say that if the GVHD was considered to be mild or moderate, the single compound treatment was effective. However, when the severity of the GVHD to be treated was, for example, considered to be severe, a single compound treatment (for example, anti-CCL24 alone) was no longer considered to be effective enough to show, for example, disease remission or a reduce in inflammatory markers. Thus, in such severe cases of immunological diseases, a person skilled in the art may consider the use of more than one compound or pharmaceutical composition as disclosed herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Cell Preparation

Umbilical cord blood mononuclear cells (UCB-MNCs) were isolated from fresh cord blood obtained from Singapore Cord Blood Bank with Ficoll-paque plus (density 1.077 g/l, GE Healthcare) using an established protocol.

Bone marrow (BM)-MSCs were obtained from the BM aspirates of healthy donors (Singapore General Hospital, Department of Hematology). It was cultured in Dulbecco's modified Eagle's Medium (DMEM) supplemented with 20% heat-inactivated Fetal Bovine Serum (FBS) (Gibco) in 3° C., 5% $CO_2$ incubator. Non-adherent cells were removed after 48 hours, and adherent cells were maintained with medium replenishment every 3-4 days until reaching to 90-100% confluence. It was passaged at 1:3 ratios using 0.05% trypsin-EDTA (Gibco) and only cells before 10 passages were used.

Human cryopreserved peripheral blood mononuclear cells (PBMCs) were obtained from healthy donors (Singapore General Hospital, Repository of Department of Hematology).

Immunosuppression of MSCs in Mixed Lymphocyte Reaction (MLR)

MLR served as an in vitro GVHD model and was initiated by co-culturing two HLA-mismatched UCB-MNCs at 15:1 effector/target (UT) ratios in StemSpan™ medium (Stem Cell Technologies) for 20 hours in 3° C., 5% $CO_2$ incubator. The mixed lymphocytes (ML) were treated with BM-MSCs by co-culture without transwell inserts (i.e. physical direct contact) or with transwell inserts (i.e. indirect bidirectional regulation via the two secretomes) or with BM-MSC-conditional medium. Transwell inserts were placed at 0.5 mm and 0.9 mm above the well bottom, and the 1-day old BM-MSC culture medium was used as conditional medium (1d-CM). Untreated MLR was used as a negative control to set the cell-mediated cytotoxicity baseline of the MLR. The cell-mediated cytotoxicity was measured by lactate dehydrogenase (LDH) cytotoxicity detection kit (Roche). Following the kit instruction, the detection plate was incubated in the dark for 20 minutes at room temperature, and absorbance was measured at 490 nm with 650 nm as reference wavelength using Benchmark Plus microplate spectrophotometer (Bio-Rad).

Detection of MSC-Modulated Cytokines

After 20 hours incubation, supernatant from cultures of ML, BM-MSCs and ML with BM-MSCs was collected and centrifuged at 400 g for 10 mins. The supernatants were analysed with the Raybio® human cytokine antibody array G series 1000 (containing 120 kinds of cytokines antibody) according to the manufacturer's instructions. Incubated slides were scanned and analysed by Axon Genepix 6.1.

Identifying Critical Factors in the MSC Secretome by FD

Twelve molecules (six upregulated proteins-OPG, CCL7, CCL8, CCL20, CXCL5 and CXCL6; four antibodies against downregulated proteins-M-CSF, IL-1β, CCL-1 and CCL24; and two control molecules-IL-10 and PGE2 (R&D systems)) were individually titrated. All the proteins and antibodies were purchased from Peprotech. For each molecule, the lowest working concentration that caused the maximum repression of cytotoxicity by MLR was used for further analysis. In order to determine the optimal combination of interested cytokines, the twelve molecules were arranged in a $2^{12}$ fractional FD table (Table 3). There were twelve factors with two levels. Level-1 meant without addition of this interested molecule, level-2 meant addition of this interested molecule with optimal working concentration. Condition-1 without addition of any interested molecules served as negative control; Condition-16 with addition of full panel of interested molecules and MLR laid on MSCs served as positive control respectively.

Based on the maximal extend attenuating cell-mediated cytotoxicity, another $2^7$ factorial FD (Table 4) was derived from Condition-6 in $2^{12}$ fractional FD, which involved IL-10, OPG, CXCL5, CXCL6, CCL20 anti-CCL1 and anti-CCL24.

Similarly, a $2^4$ full FD (Table 5) was further derived from Condition-6 in $2^7$ fractional FD, which involved OPG, CXCL5, anti-CCL1 and anti-CCL24.

Maximum Tolerance Dose (MTD) Study

Two doses of anti-CCL24 antibody and CXCL5 chemokine were administrated to 8-10 week-old healthy NSG mice by intravenous (IV) injection at day-1 and day-3 of every week. Injection dose was gradually increased at the beginning of every week (Table 6). The mice body weight and survival were monitored every other day for consecutive 30 days.

Mice

Non-obese diabetic/severe combined immunodeficient-IL2R gamma$^{null}$ (NOD.Cg-Prkdc$^{scid}$ Il2rg$^{tm1Wjl}$/SzJ, NSG) mice and MLR/MpJ-Fas$^{lpr}$/J (Fas$^{lpr}$) mice were purchased from Jackson Laboratories. Mice were housed in SingHealth Experimental Medicine Centre and all animal experiments were conducted with the approval of SingHealth Institutional Animal Care and Use Committee (IACUC). For GVHD induction, the age of NSG mice used in all experiments was between 8-10 weeks. For SLE, only female Fas$^{lpr}$ mice were used and the average age of auto-onset of disease was around (14-16)-week-old.

GVHD Induction and Treatment

Moderate and severe xenogeneic GVHD mouse model was induced by injecting $200 \times 10^6$ cells/kg and $400 \times 10^6$ cells/kg of human cryopreserved PBMCs to NSG mice respectively by IV injection via tail vein. 240 cGy of irradiation was given to the mice 3-4 hours before the transplantation. NSG mice showed onset of GVHD on 10-12 days post-transplantation (PT). Hence, treatment with 2F cocktail, single format of CXCL5 and anti-CCL24 antibody was given on day-10, day-14, day-17 and day-21 PT. NSG mice injected with dPBS were used as negative control. Mice injected with BM-MSCs ($10 \times 10^6$ cells/kg, single injection on day-10) and CsA (15 mg/kg, Novartis) were used as positive control. Injection volume was normalized to the body weight of the mice. Mouse survival was monitored daily, while clinical scoring was done every three days. 30-40 ul of mouse peripheral blood (PB) was collected from tail vein every 3 days, from day 18 onwards until day 36 post-treatment. Mouse plasma and isolated cells from PB, marrow and spleen were used for luminex assay (Bio-rad) and flow cytometry analysis (CyAN, Beckman coulter). As used herein, the term "PT" stands for post-transplantation of human PBMCs. At day 0, human PBMCs were transplanted into NSG mice to create the referenced GVHD model. The onset of GVHD is took place around day 10 to day 12 PT. Treatment of the sick mice commenced on day 10, day 14, day 17 and day 21 PT, and samples were taken from the mice on day 18, 21, 24, 27, 30, 33 and 36 PT.

Systemic Lupus Erythematosus (SLE) Treatment

MLR/MpJ-Fas$^{lpr}$/J (Fas$^{lpr}$) mice, homozygous for the lymphoproliferation spontaneous mutation, show systemic autoimmunity, massive lymphadenopathy associated with proliferation of aberrant T cells, arthritis, and immune complex glomerulonephrosis. Because of the manifestation similarity between Fas$^{lpr}$ mice and SLE patients, Fas$^{lpr}$ mice can be used as SLE mouse model.

Fas$^{lpr}$ mice automatically showed onset of disease around 16 weeks of age, on average. 10 times of weekly 2FC treatment was given on 16-week-old mice. Fourteen doses of 2F cocktail treatment were weekly given to 16-week-old (16 w) female Fas$^{lpr}$ mice. $5-10 \times 10^6$ cells/kg of BM-MSCs and dPBS were used as positive and negative control. The efficacy of 2F cocktail in SLE was evaluated by the improvement of mice survival, kidney function and reduction of autoantibodies secretion. Mice plasma and urine were collected on 14 w-, 18 w-, 22 w-, 26 w- and 30 w-old mice. Autoantibodies secretion was measured by anti-dsDNA Ig's (A+G+M) ELISA kit (alpha diagnostic international). Kidney function was assessed by urine albumin-to-creatinine ratio (ACR). Mouse albumin ELISA kit was from abcam, creatinine colorimetric assay kit was from Cayman chemical. Autoantibody and ACR detections followed the standard protocol provided by the manufacturer.

Clinical and Histological Scoring

Mouse survival was monitored daily and clinical score (for GVHD) was monitored every three days. The assessment of clinical GVHD index was based on five parameters: weight loss, posture, activity, fur texture and skin integrity, giving a maximum index of 10. At experimental end-point on day30 post-treatment, histological evaluation was performed on representative mice on the following tissues: skin, small intestine and kidney with Haematoxylin and Eosin (H&E) stain. Key histological parameters assessed were different for each tissue type according to accepted published criteria for acute GVHD in the different organ systems. Basal vacuolar change, spongiosis and lymphocytic satelittosis were graded for skin; crypt apoptosis, lymphocytic inflammation and intraepithelial lymphocytosis was graded for small intestine; and interstitial inflammation, tubulitis and arterial changes were graded for kidney. All parameters were graded with 4 tiers (none, mild, moderate and severe) and given a score of 0-3, giving a maximum index of 27 (Table 7). The slides were scored in blinded fashion by a single observer.

ELISA and Luminex Assay

Anti-dsDNA antibody concentration in Fas$^{lpr}$ mice plasma was determined using Mouse Anti-dsDNA Antibodies Total Ig ELISA kit (Alpha Diagnostic). 150-200 ul of mouse peripheral blood was harvested by cheek bleeding every 4 weeks from mice aged 14-week-old onwards until 26-weeks old. 4,000 times diluted Fas$^{lpr}$ mice plasma samples were incubated in the 96-well-plate for 1 hour. Then anti-Mouse Ig HRP conjugate was added and incubated for 30 minutes. TMB substrate was added for 15 minutes and finally the reaction was halted with stop solution. Five complete wash steps were required between each incubation step. The plate was read on Bio Rad microplate spectrometer at 450 nm.

Using luminex technology, multiple analytes can be detected simultaneously in the same sample. Circulating human source cytokines/chemokines were measured using a Bio-plex Pro Human Cytokine 17-plex kit (Bio-rad). It included analytes of G-CSF, GM-CSF, IFN-γ, IL-1β, IL-2, IL-4, IL-5, IL-6, IL-7, IL-8, IL-10, IL-12, IL-13, IL-17A, MCP-1, MIP-1β and TNF-α in the analysis. Following the standard protocol, 16 times diluted plasma samples were incubated with magnetic beads for 2 hours, the with detection antibodies for 1 hour and finally with streptavidin-PE for 10 minutes at room temperature. Three complete wash steps were required between each incubation step. The plate was read on Milliplex Analyzer (Millipore) with Luminex xPONENT software.

Albumin and Creatinine Detection

Kidney function damage of Faslpr mice was evaluated by measuring the changes of urinary albumin to creatinine ratio (ACR). 20-50 ul of urine was harvested by bladder massage every 4 weeks from 14-week-old onwards until 26-week-old. Albumin concentration was detected by Mouse Albumin ELISA kit (Abcam). Following the standard protocol, 100,000 times diluted $Fas^{lpr}$ mice urine samples were incubated in the primary antibody coated 96-well-plate for 2 hours, biotinylated antibody for 1 hour, streptavidin-peroxidase for 30 minutes, chromogen for 15 minutes and finally with the stop solution. Five times complete wash were required between each incubation step. The plate was read on Bio Rad microplate spectrometer at 450 nm.

Creatinine level was detected by Jaffe's reaction using Creatinine Colorimetric Assay kit (Cayman). Following the standard protocol, 20 times diluted FasIpr mice urine samples and alkaline picrate solution was added to the 96-well-plate. Plate was incubated in room temperature for 10 minutes and read on Bio Rad microplate spectrometer at 490 nm.

Flow Cytometry Analysis

Cells isolated from NSG mouse peripheral blood (PB) harvested from tail vein, BM and spleen were subjected to flow cytometric analysis using CyAN (Beckman coulter) with Summit software. For cell surface markers, the following antibodies were used: hCD45-PE-Cy7 (H130), hCD3-ECD (UCHT1) (Beckman coulter), hCD4-PerCP-Cy5.5 (SK3), hCD8-APC (RPA-T8), hCD56-FITC (NCAM16.2), hCD25-PE-Cy7 (M-A251), hFoxP3-PE (259D/C7), hIFN-γ-BV421 (4S.B3), hIL-17A-AF647 (N49-653), hCD68-BV421 (Y1/82A), hCD19-FITC (H1B19), hCD34-BV421 (581); and mCD45-AF700 (30-F11), mCD45-FITC (30F11) (Miltenyi Biotec), mCD11b-APC (M1/70), Ly6G-PC7 (1A8).

For intracellular staining, cells were stimulated with 50 ng/ml of PMA (Sigma-Aldrich) and 1 µg/ml of ionomycin (Sigma-Aldrich) overnight (12-16 hours) at 3° C. 3 µg/ml of brefeldin A (Sigma-Aldrich) was added one hour after incubation. Activated cells were further fixed and permeabilized by Fixation/Permeabilization solution (Miltenyi Biotec) for 45 minutes at 2-8° C. Then the cells were washed with permeabilization buffer two times and stained with intracellular antibodies for 30 minutes at 2-8° C. in the dark.

For cells isolated from $Fas^{lpr}$ mouse spleen, mesenteric lymph node and thymus, the following antibodies were used: mCD45-PE (30F11), mCD19-FITC (1D3), mCD3-PC7 (17A2), mCD4-APC-CY7 (GK1.5), mCD8a-V500 (53-6.7), mCD11c-Percp-cy5.5 (HL3), mCD49b-APC (DX5), mLy6G-PC-Cy7 (1A8), mCD11b-APC (M1/70) and mCD1d-BB515 (1B1). All antibodies were purchased from BD Biosciences unless otherwise specified.

Statistical Analysis

Factorial design experiments were analysed using ANOVA. Student paired t-test was used to do the significance analysis. p<0.05 was considered statistically significant. The overall trend difference was compared by means of generalized estimating equation (GEE) model.

MSCs Modulate Allogenic Immune Reactions Through Paracrine Factors

Conditioned medium from a 24 h, pure BM-MSC culture was able to reduce cell-mediated cytotoxicity to 83.9±8.1% in in an in vitro GVHD model-MLR (FIG. 1). Cytotoxicity was further reduced when the BM-MSC was co-cultured with the MLs in transwell inserts; suggesting that the BM-MSC secretome might be partially regulated by the MLs. The degree of reduction in cytotoxicity is influenced by the physical distance between the two cell types. It was reduced to 62.2±3.2% at 0.9 mm and 47.5±6.5% at 0.5 mm. The maximum reduction occurred when the cells were in physical direct contact (27.9±3.6%). These results indicate that the immunosuppressive effect of MSCs is partly or wholly paracrine in nature and is negatively correlated to the separation between the MLs and MSCs.

MSC-Secreted Paracrine Factors Were Elucidated by Cytokine Antibody Array

Figure 2:
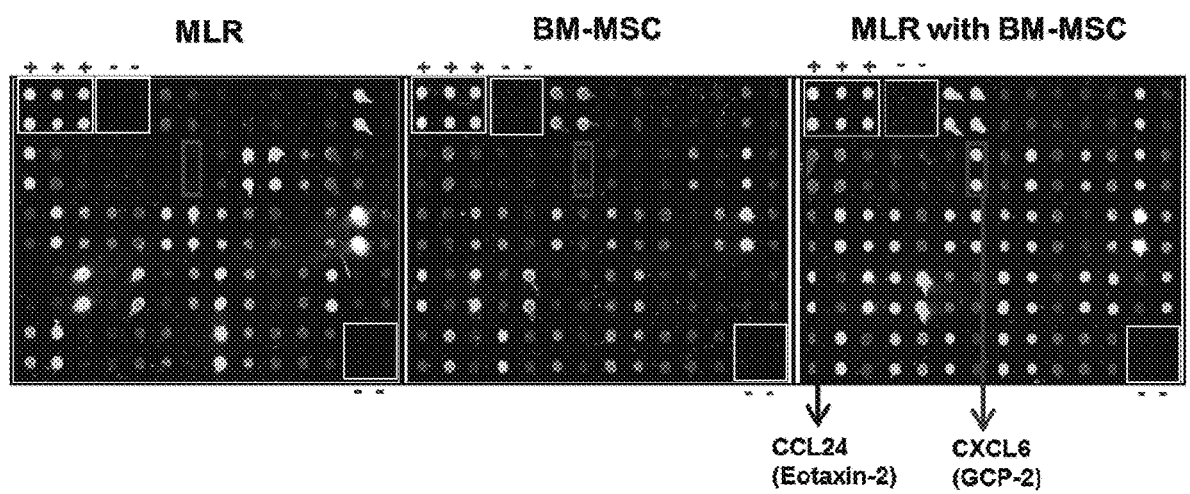
FIG. 2 shows images of a cytokine antibody array assay, whereby supernatant from cultures of MLR, BM-MSCs and MLR with BM-MSCs was collected and applied on Raybio human cytokine antibody array G series 1000 (containing 120 kinds of cytokines antibody) according to the manufacturer's instructions. Incubated slides were scanned and analysed by Axon Genepix 6.1. Positive and negative control wells were marked by white boxes, while wells with more than 3-fold change in protein expression level were marked by grey box (upregulated) and black box (downregulated).

Factors that presented in the BM-MSC/ML co-culture and in single cultures were identified using a cytokine antibody array (FIG. 2). With a selection criterion of at least a three-fold change in cytokine expression levels, five upregulated proteins were identified, namely CCL20, CCL8, CXCL5, OPG and CXCL6, as well as three downregulated proteins, IL-1β, CCL1and CCL24 (Table 2). In order to ascertain that relevant factors were not missed by the arbitrary three-fold cut-off, 2 factors with a fold-change between 2 and 3 were randomly chosen (CCL7 and M-CSF) and added to the subsequent validation experiments.

Optimal Working Concentration of Immunosuppression Relevant Factors was Determined For further studies to identify critical factors amongst the 10 candidates, the working concentration of each upregulated factors and antibody against downregulated factors had to be established. Dose response curves of cytotoxicity repression in MLR were generated and the lowest concentration to general maximum repression was selected as the working concentration (FIG. 3). PGE2 and IL-10 were reported to be effective in modulating cell proliferation and cytotoxicity on $CD4^+$ helper T cells, $CD8^+$ cytotoxic T cells and nature killer cells; hence they were included as control molecules. The optimal in vitro working concentrations were: 50 ng/ml of CCL20, 10 ng/ml of CXCL6, 50 ng/ml of CCL7, 10 ng/ml of CCL8, 10 ng/ml of OPG, 10 ng/ml of IL-10, 50 ng/ml of CXCL5, 2 µM of PGE2 and 2 µg/ml of anti-CCL1, 1 µg/ml of anti-IL-1β, 1 µg/ml of anti-M-CSF, 2 µg/ml of anti-CCL24 antibody respectively Among these twelve factors, anti-CCL1 antibody affected the highest level of cytotoxicity repression (42.7±4.1%). But it was still significantly higher than the 22.7±2.8% from MLR with direct contact between BM-MSC and ML (p<0.001). This indicated that inhibition or promotion of any single factor from the list could not fully mimic the immunosuppressive effect of MSCs. This means that, while single factors were shown to be effective, they are not considered to be as effective as the combinations, when comparing the resulting immunosuppressive effect. Having said that, it is also noted, as mentioned previously in this application, that the severity of the disease to be treated has an effect on the efficacy of the treatment chosen. Hence, without being bound by theory, it is thought that MSC modulated immunosuppression through a combination of factors, of which the optimal combinations were identified and validated using by factorial design.

Optimal Combination of Immunosuppression Relevant Factors Were Determined by FD

Figure 4:
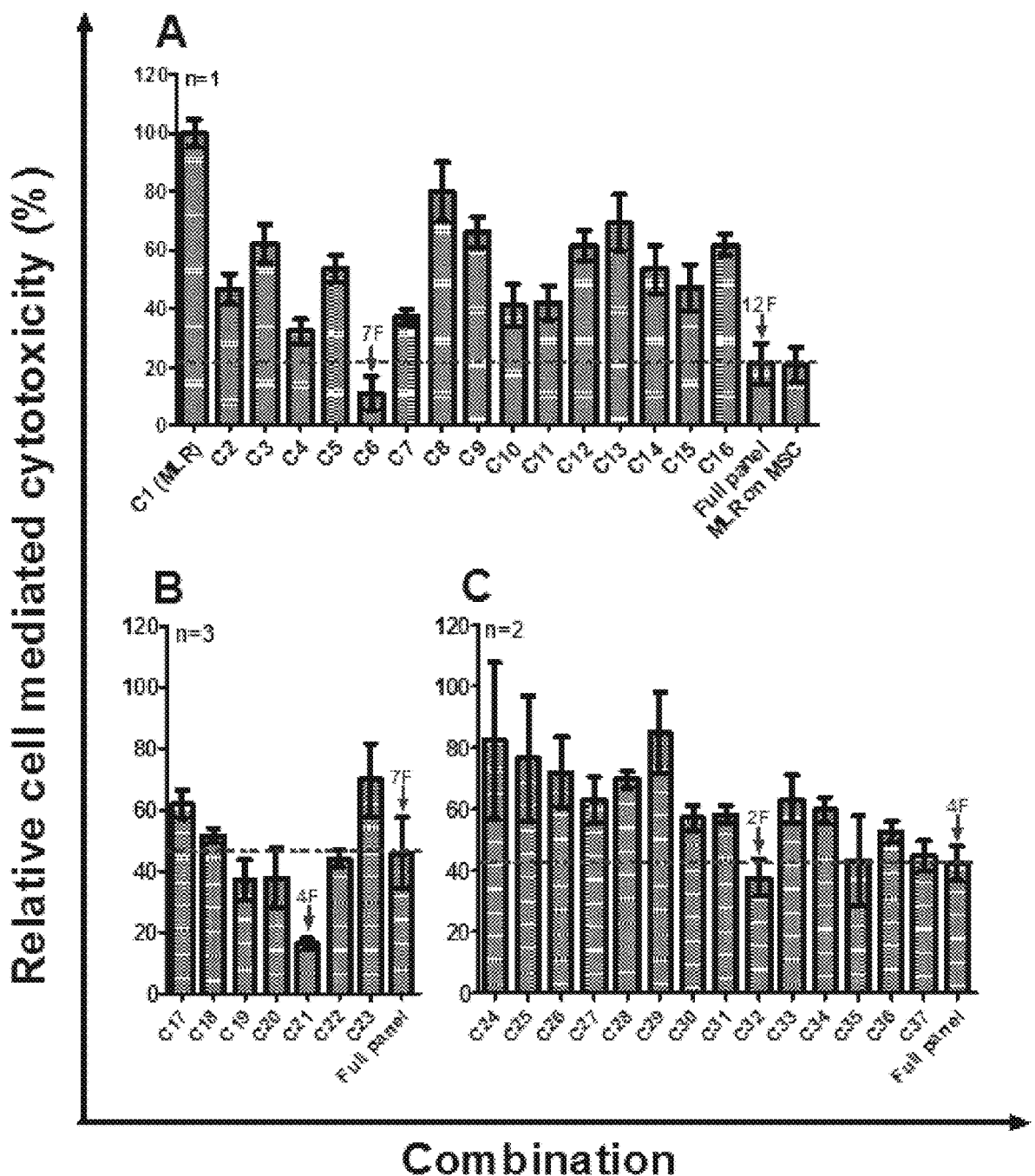
FIG. 4 shows column graphs depicting data of the efficacy of the combination of determined factors used in optimal soluble factor cocktails, which was determined by serial factorial design experiments (FDs). (A) The full panel of 12 factors were screened in a $2^{12}$ factional FD (n=1). Condition-6 (C6) containing 7 factors was more effective than full panel control and MSC physical contact in repressing cell mediated cytotoxicity ($p<0.05$). (B) A second $2^7$ fractional FD identified C6 with 4 factors was even more effective than full panel control in repressing cell mediated cytotoxicity (n=3, $p<0.05$). (C) These 4 factors were further tested in a $2^4$ full FD (n=2). C10 containing two factors-CXCL5 and anti-CCL24 antibody exhibited equivalent effect in repressing cell mediated cytotoxicity as compared to 4 factor full panel control. Results were expressed as mean±S.E. when n≥2. Results were expressed as mean±S.D. when n<2.

Factorial design is an efficient method for determining the effects of multiple variables on a single response. It can reduce the number of experiments by studying multiple factors simultaneously. Here, a $2^{12}$ fractional FD was used to determine the optimal combination and relative importance of 12 factors of interest (Table 3). The relative cell-mediated cytotoxicity of $2^{12}$ fractional FD was showed in FIG. 4A. The optimal combination was C6, which comprised seven factors: CCL20, CXCL6, OPG, IL-10 and CXCL5 protein as well as anti-CCL1 and anti-CCL24 antibodies, which reduced the relative cell-mediated cytotoxicity to 11.1±5.8%. It was even more effective than the full panel control (21.1±6.9%) and the BM-MSC co-culture with direct contact (20.7±6.0%) (p<0.05).

From variance analysis, the relative importance of these twelve factors in immune suppression was determined. anti-CCL24 (F=11.09)>IL-10 (F=4.38)>OPG (F=2.92)> CXCL5 (F=2.62)>anti-IL-1β (F=2.52)>CXCL6 (F=2.14)> anti-M-CSF (F=2.09)>anti-CCL1 (F=1.89)>CCL20 (F=0.48)>PGE2 (F=0.12)>CCL7 (F=0.10)>CCL8 (F=0.09) (p<0.05, $F_{statistic\ cut-off}$=10.10). There was significant impact on immunosuppression when F value was more than 10.10. Hence, only anti-CCL24 antibody significantly affected cell mediated cytotoxicity as compared to others.

In addition, anti-M-CSF ($7^{th}$) and CCL7 ($11^{th}$) were not included in C21 and had F statistics that were below the cut-off of 10.10. This indicated that the selection of candidate factors was sufficiently stringent.

In order to eliminate unnecessary factors in C6 ($2^{12}$ FD), the seven factors were subjected to another round of fractional FD experiment ($2^7$) (Table 4). The relative cell-mediated cytotoxicity of $2^7$ fractional FD was shown in FIG. 4B. The optimal combination was C21, which consisted of four factors: CXCL5, OPG protein and anti-CCL1, anti-CCL24 antibodies. It could reduce the relative cell-mediated cytotoxicity to 16.1±2.1% (n=3), which is superior to 45.8±14.3% in the full panel control.

These four factors were further analysed in a full FD (Table 5). The relative cell-mediated cytotoxicity was shown in FIG. 4C. The optimal combination was C32, which consisted of only two factors: CXCL5 and anti-CCL24 antibody. It could suppress the relative cell-mediated cytotoxicity to 37.7±6.2%, which is comparable to 44.7±4.9% in the full panel control C38. Thus, through serial FDs, a two factor (2F)-cocktail comprising CXCL5 and anti-CCL24 antibody was finally established.

Safe Administration Dose, Side Effect on Neutrophil and Red Blood Cell (RBC) Count as Well as Toxicity Test Before validating the immunosuppressive effect of the 2F cocktail in mice, the safety dose of each factor needs to be established.

Figure 5:
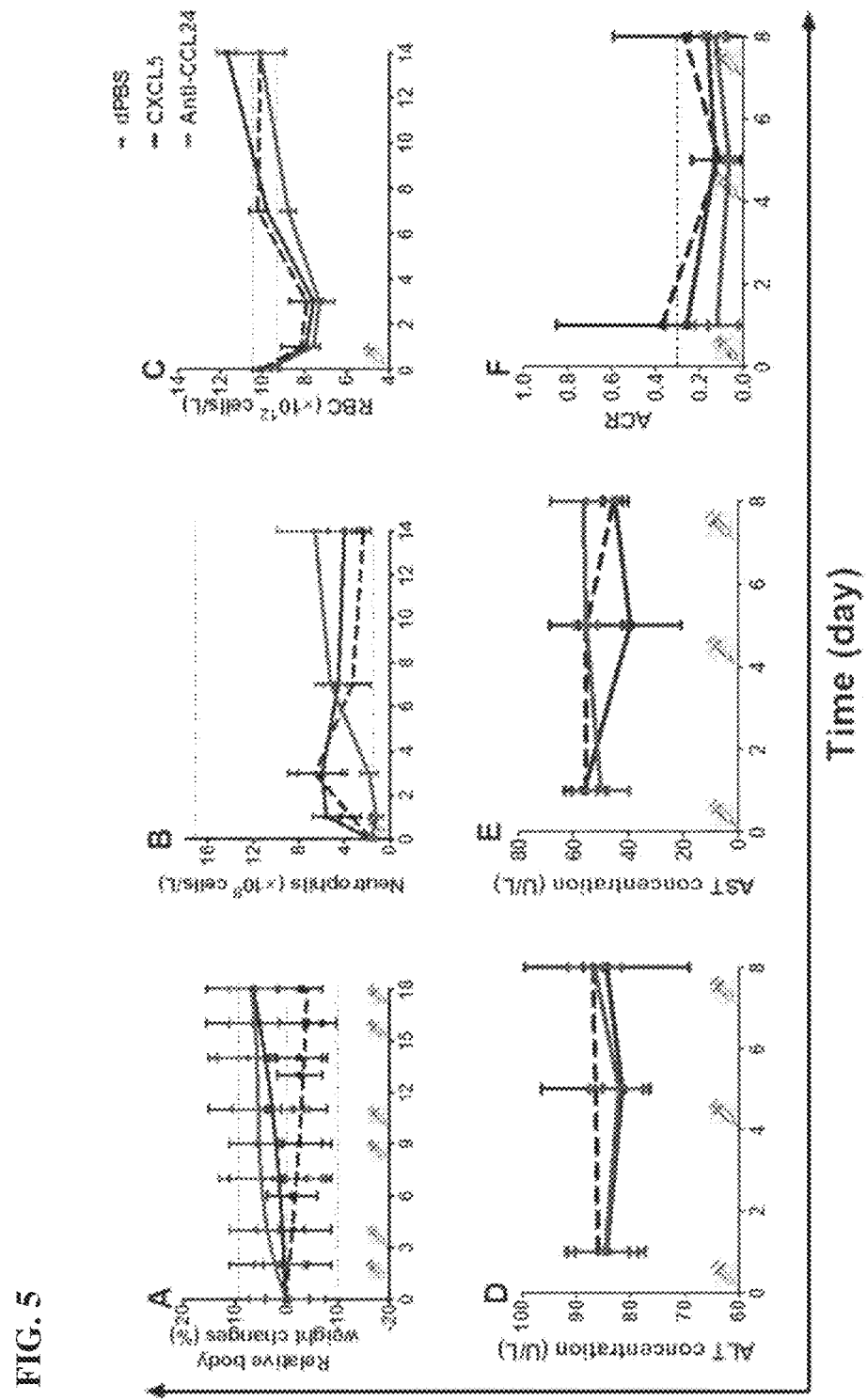
FIG. 5 shows line graphs depicting the relative weight change, side effect on neutrophil and red blood cell count and toxicity in liver and kidney when mice were treated with CXCL5 and anti-CCL24 antibody. (A) Body weight changes. NSG mice were treated with CXCL5 and anti-CCL24 antibody twice weekly with gradually increasing dose (3 mice were used in each group). (B & C) Side effect on neutrophil and red blood cell count. ICR mice treated with dPBS, CXCL5 and anti-CCL24 antibody were bled and a blood count was performed on day1, day3, day7 and day14 post-treatment (4 male mice were used for each group). (D & E & F) Liver and kidney toxicity. ICR mice were treated with dPBS, CXCL5 and anti-CCL24 antibody on day0, day4 and day7. Mice peripheral blood by cheek bleeding and urine were harvested on day1, day5 and day8. Alanine transaminase (ALT) and aspartate transaminase (AST or SGOT) concentration in plasma were determined by ALT and AST activity assay kit. Both alanine transaminase and aspartate transaminase are enzyme associated with the liver and are therefore used as clinical marker for liver health. Albumin creatinine ratio (ACR) in urine was determined by Mouse Albumin ELISA kit and Jaffe's reaction using Creatinine Colorimetric Assay kit (3 female ICR mice were used for each group).

CXCL5 and anti-CCL24 antibody were administered to 8 to 10 week old healthy NSG mice (Table 6). The survival and body weight changes were monitored for 18 days (FIG. 5A). The body weight stably maintained when mice were treated with CXCL5 and anti-CCL24 antibody, which was higher than mice treated with dPBS. All the mice survived to the end of the experiment (18 days). Mice injected with either of the factors (at all doses) did not show abnormal clinical symptoms during the experiment. Overall, administration of the 6 µg/ml of anti-CCL24 and 200 ng/ml of CXCL5 twice per week was well-tolerated and was deemed safe to use for subsequent in vivo studies. Overall, administration of the 6 µg/ml of anti-CCL24 and 200 ng/ml of CXCL5 twice per week was well-tolerated and was deemed safe to use for subsequent in vivo studies.

The side effect on neutrophils and RBC count were evaluated in male ICR mice. Administration of CXCL5 or anti-CCL24 antibody did not alter neutrophil and RBC count, it still kept them in normal range and there was no significant difference between mice treated with single factor and dPBS (FIGS. 5B and 5C).

The toxicity of these two factors was also tested in female ICR mice. Administration of these two factors did not show any toxicity to mice liver and kidney. There was no significant difference in ALT, AST expression level in liver and ACR in kidney between mice treated with single factor and dPBS (FIGS. 5D, 5E and 5F).

2F Cocktail Treatment Exhibited Tremendous Immunosuppressive Capacity in Severe GVHD In order to validate the efficacy of the 2F cocktail in immunosuppression, four doses were administered to mice after the onset of GVHD on Day-10, Day-14, Day-17 and Day-21 post-transplant (PT).

Figure 6:
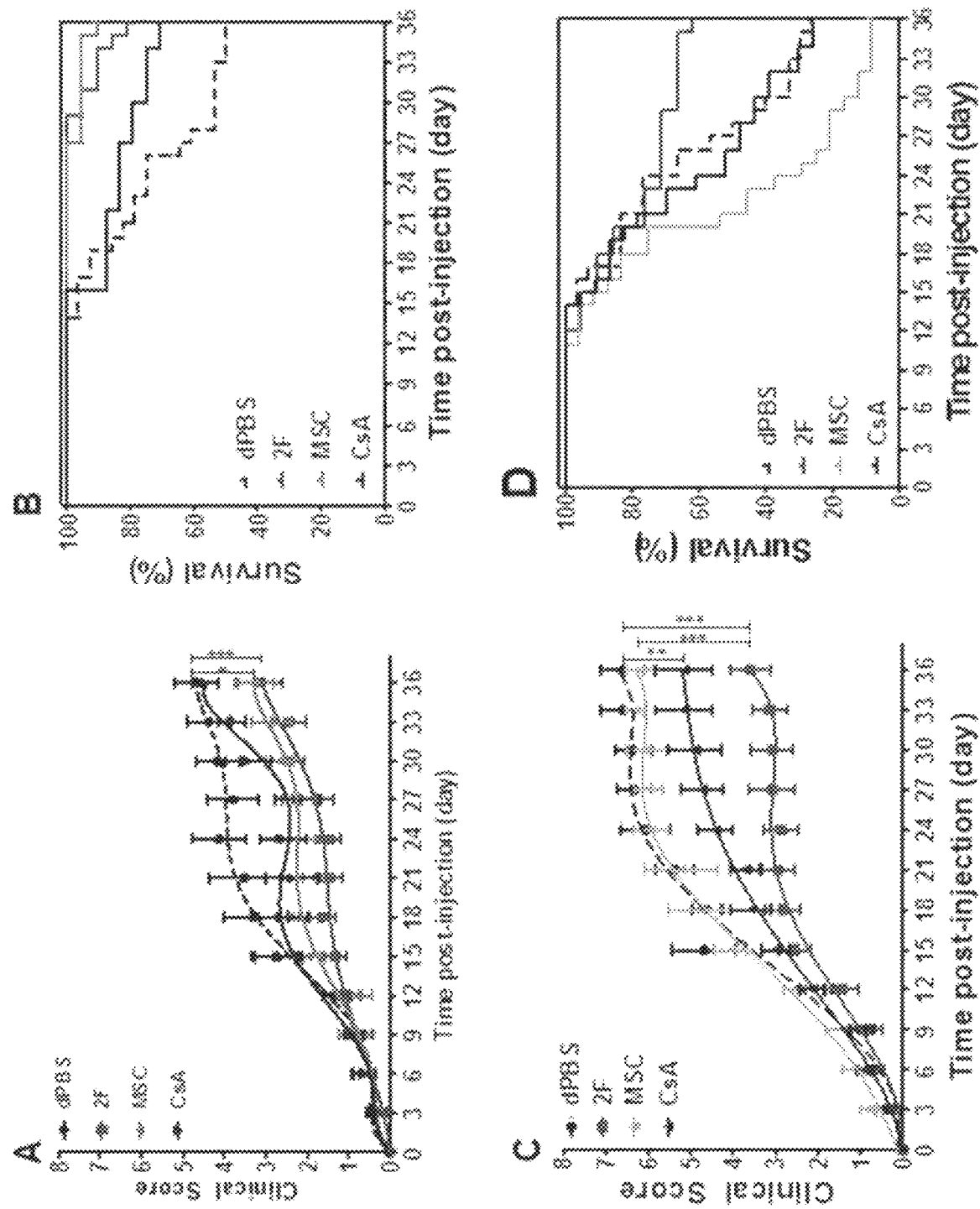
FIG. 6 shows line graphs depicting data showing that the 2F cocktail treatment (anti-CCL24 antibody and CXCL5) ameliorated GVHD symptoms and prolonged survival. (A) Clinical scores and (B) Survival curve with mice in moderate GVHD (n=5; $N_{dPBS}$=28 mice, $N_{2F}$=21 mice, $N_{MSC}$=21 mice, $N_{CsA}$=23 mice). (C) Clinical scores and (D) Survival curve with mice in severe GVHD model (n=5; $N_{dPBS}$=30 mice, $N_{2F}$=21 mice, $N_{MSC}$=24 mice, $N_{CsA}$=23 mice). Results were expressed as mean±SE. The overall trend difference between different treatments was compared by means of generalized estimating equation (GEE) model (*p<0.05; p<0.005; *p<0.001).

In moderate GVHD, the 2F cocktail improved 36-day survival from 61.1% with moderate symptoms to 88.9% with mild symptoms (dPBS: 11/18 mice; 2F: 16/18 mice, (p<0.05)). This was comparable to BM-MSCs (88.9%, 16/18 mice) and CsA (83.3%, 14/17 mice), a conventional clinical immunosuppressant (FIGS. 6A and 6B, Table 7). However, in severe GVHD, the 2F cocktail improved 36-day survival from 19.0% with severe symptoms to 61.9% with mild symptoms (dPBS: 4/21 mice; 2F: 13/21 mice, (p<0.01)). This was significantly better than BM-MSC (8.3%, 2/24 mice (p<0.001)) and CsA (26.1%, 6/23 mice (p<0.05)) (FIGS. 6C and 6D).

Figure 7:
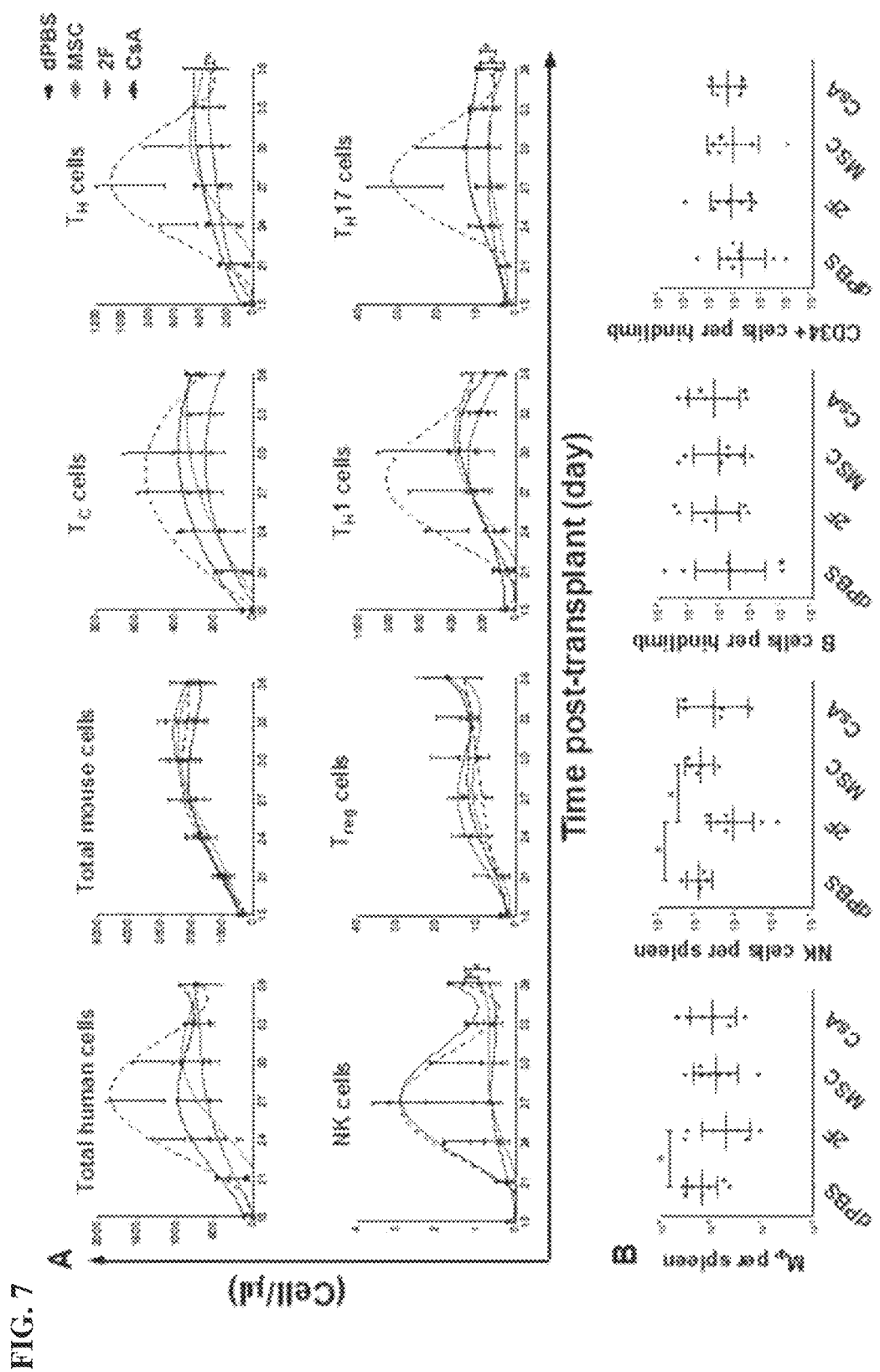
FIG. 7 shows line and scatter plots of data showing that the 2F cocktail (anti-CCL24 antibody and CXCL5) suppresses the proliferation and differentiation of effector cells, but not affect HSCs reconstitution. (A) Effector cell population changes in peripheral blood are shown as line graphs. 30-40 μl of mouse peripheral blood was harvested from the tail every 3 days from Day-18 onwards until Day-36 PT. Effector cell population changes was monitored by flow cytometry. Results were expressed as mean±S.E. (n=5). (B) Cell population changes in spleen and bone marrow at Day-40 PT shown as scatter plots. Results were expressed as mean with 95% CI.

The 2F Cocktail Ameliorated GVHD Through Suppressing the Proliferation and Differentiation of Multiple Effector Cells In moderate GVHD, the 2F cocktail treatment reduced the proliferation and differentiation of helper T cells (especially for Th1 and Th17 cells) and NK cells in the circulation, and macrophages in the spleen, but did not reduce CTLs and B cells and increase regulatory T cells (Tregs) (FIG. 7).

Figure 8:
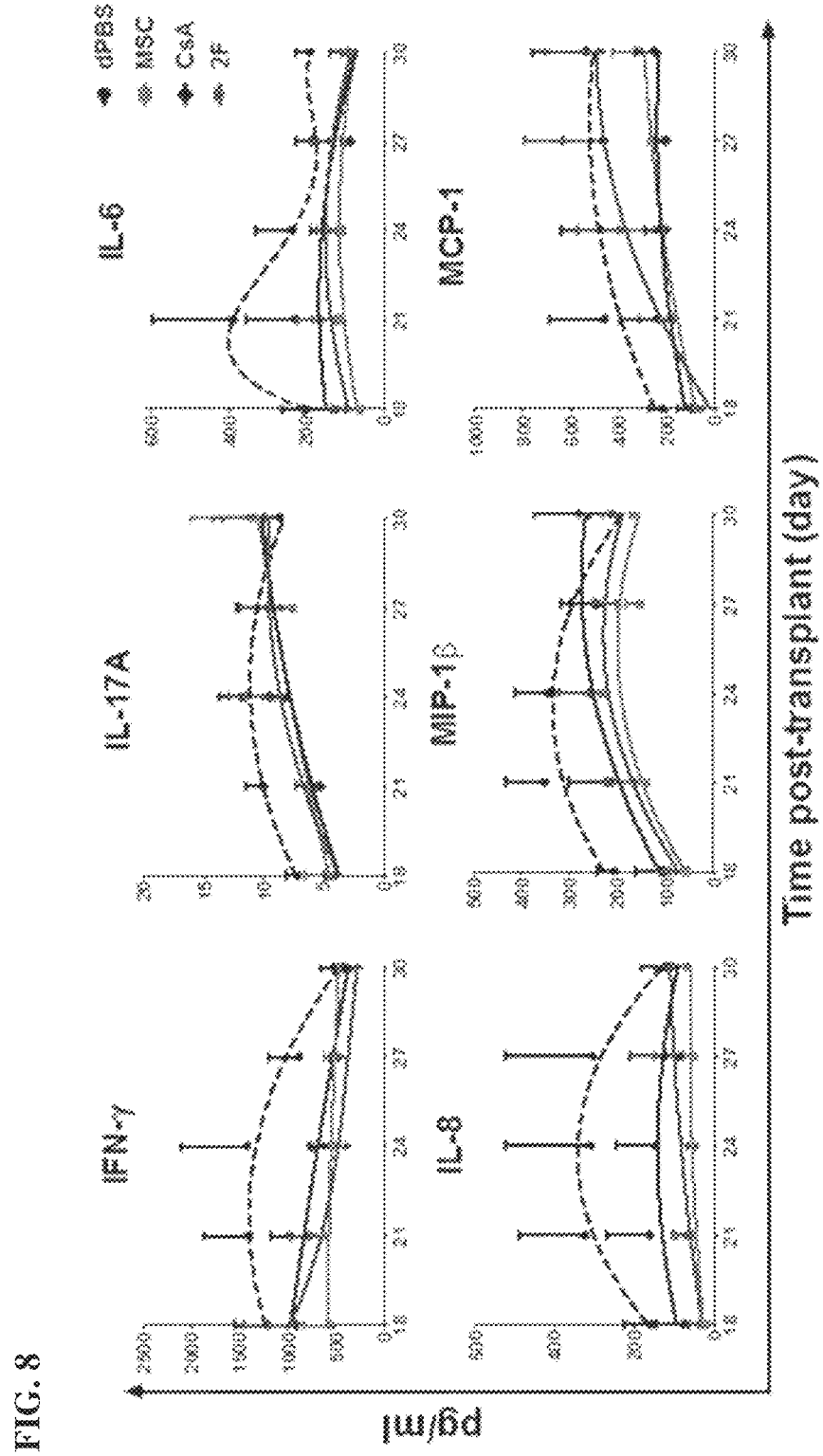
FIG. 8 shows line graphs depicting data showing that the 2F cocktail (anti-CCL24 antibody and CXCL5) was superior to MSCs and CsA in suppression of human pro-inflammatory cytokines. Plasma isolated from mouse peripheral blood was used for protein assay by Luminex with a 17-plex human cytokine kit. Results were expressed as mean±SD. The profile of different treatments was compared by means of a generalized estimating equation (GEE) model (*,p<0.0167; **,p<0.0033, for multiple comparisons).

Concurrently, it also reduced pro-inflammatory cytokine IFN-γ, IL-6, IL-8, IL-17A, MIP-1β and MCP-1 secretion in the circulation (FIG. 8). These 2F-elicited changes did not affect the reconstitution of CD34+ human hematopoietic stem/progenitor cells (HSCs/HPCs) in the bone marrow.

Anti-CCL24 and CXCL5 Affect Immunosuppression in a Concerted Manner

Figure 9:
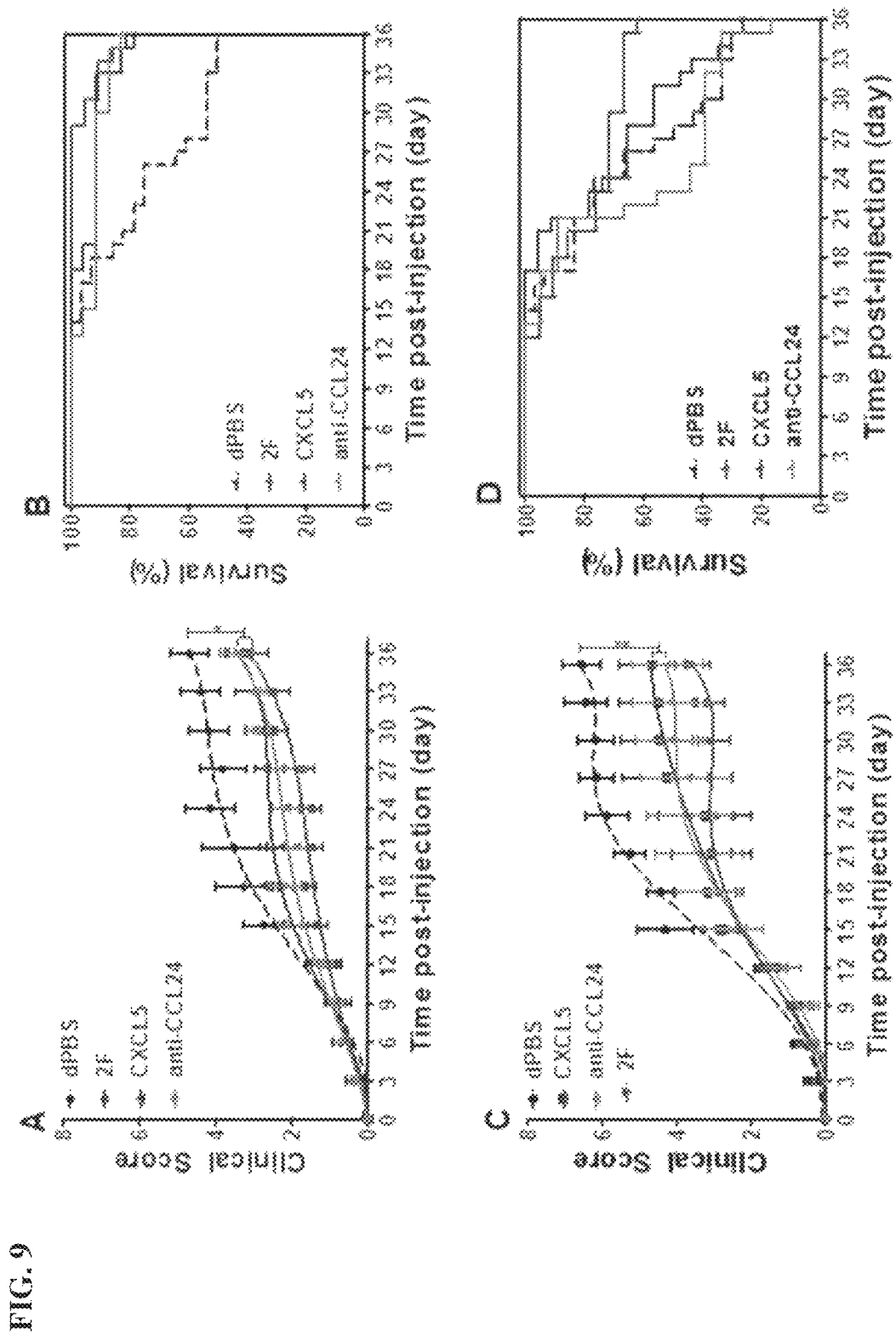
FIG. 9 shows line graphs and Kaplan-Meier curves depicting data that showing a Synergistic effect observed in severe GVHD model. (A) Clinical scores and (B) Kaplan-Meier survival curve of mice with moderate GVHD (n=5; $N_{dPBS}$=28 mice, $N_{2F}$=21 mice, $N_{CXCL5}$=23 mice, $N_{anti-CCL24}$=23 mice). (C) Clinical scores and (D) Kaplan-Meier survival curve of mice with severe GVHD (n=5; $N_{dPBS}$=30 mice, $N_{2F}$=21 mice, $N_{CXCL5}$=23 mice, $N_{anti-CCL24}$=18 mice). Results were expressed as mean±SE. The overall trend difference between different treatments was compared by means of generalized estimating equation (GEE) model (*p<0.05; p<0.005; *p<0.001).
Figure 10:
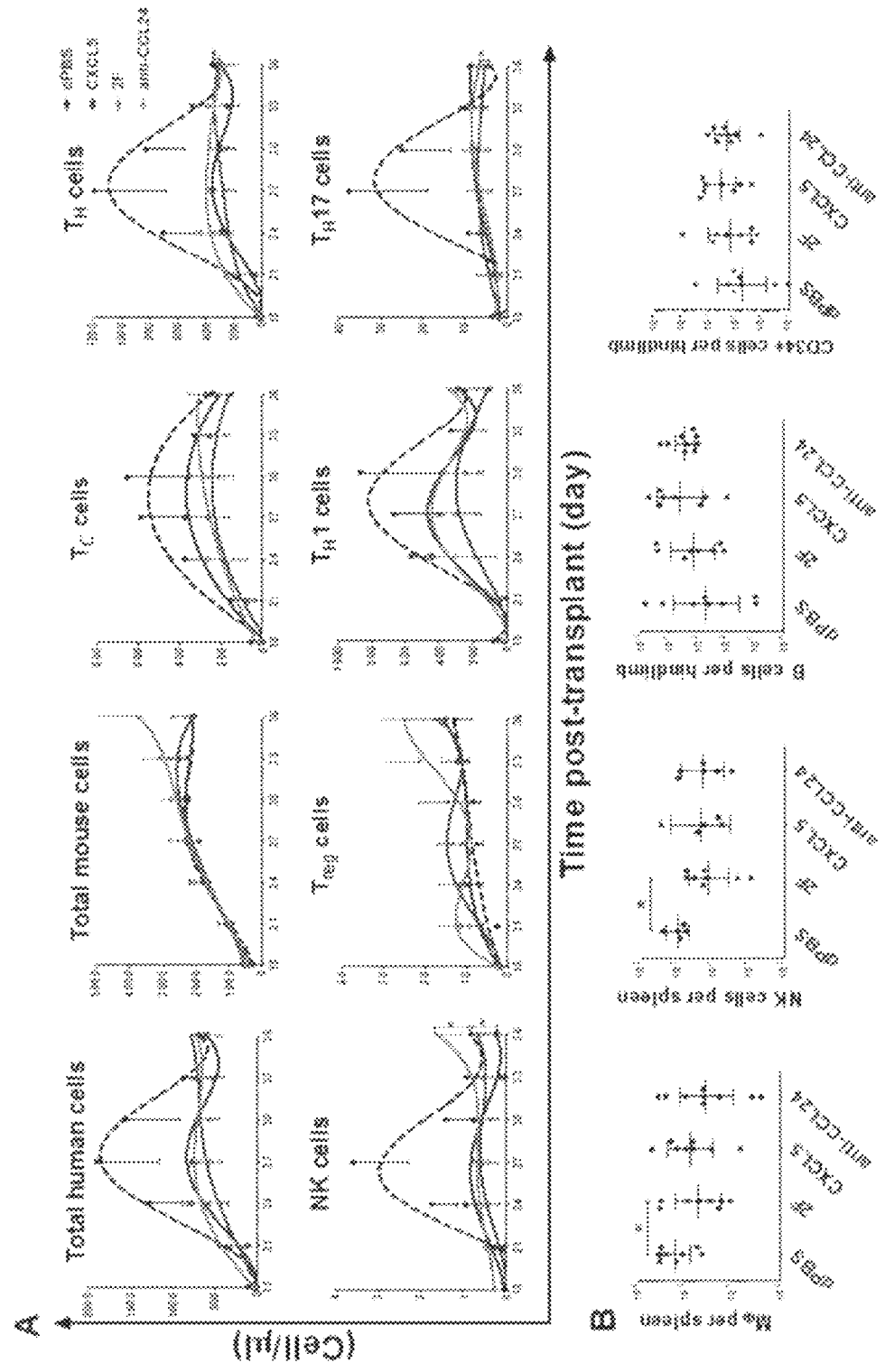
FIG. 10 shows data indicating that a single factor was comparable to 2F cocktail in suppression of human effector cells proliferation and differentiation. (A) shows line graphs showing data that effector cell population changes in peripheral blood. 30-40 ul of mouse peripheral blood was harvested from the tail every 3 days from Day-18 onwards until Day-36 PT. Effector cell population changes was monitored by flow cytometry. Results were expressed as mean±S.E. (n=5). (B) shows scatter plots of data points indicating cell population changes in spleen and bone marrow at Day-40 PT. Results were expressed as mean with 95% CI (confidence interval).
Figure 11:
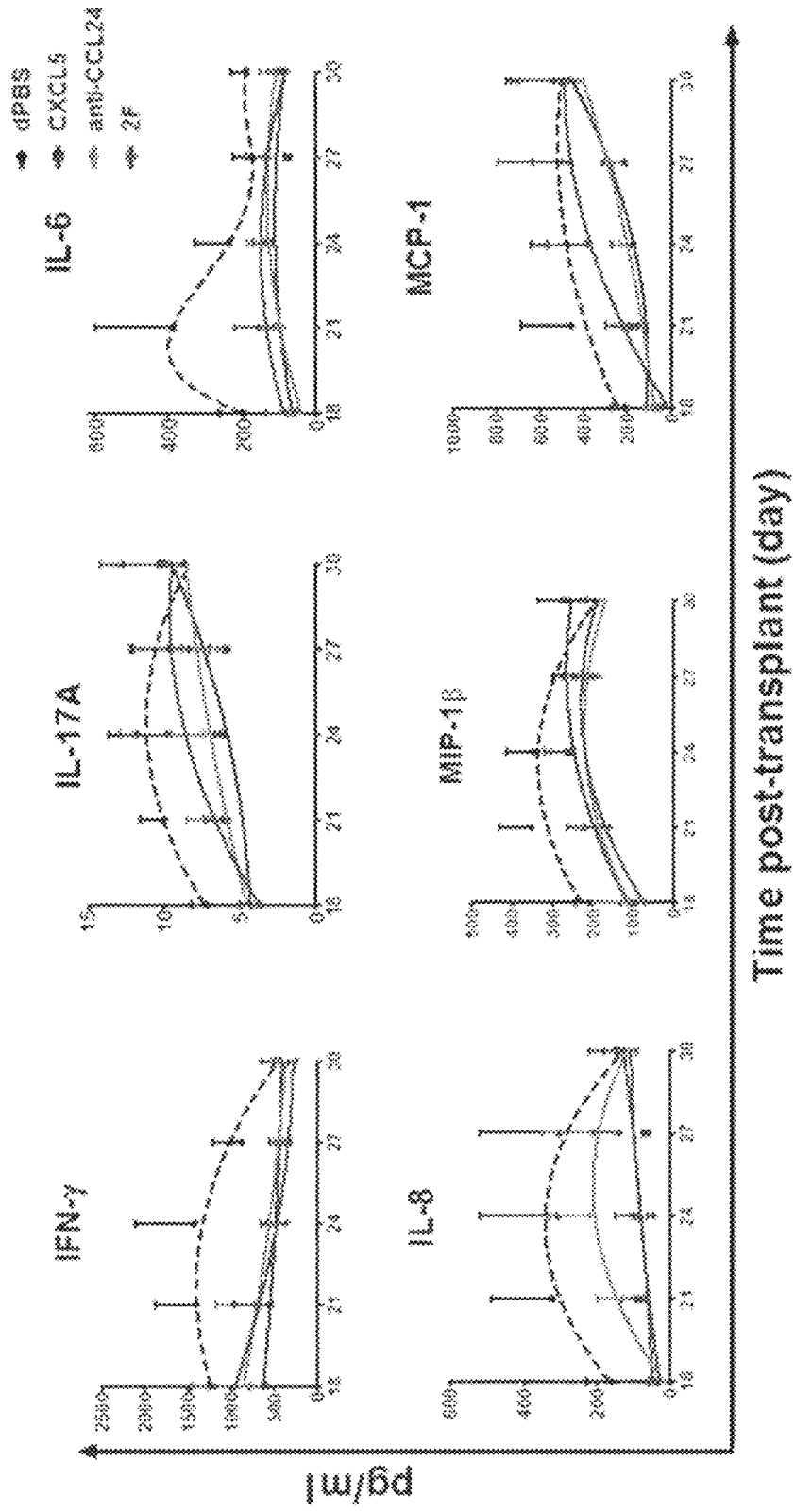
FIG. 11 provides data in the form of line curves, showing that either one of the components of the 2F cocktail was sufficient to suppress human pro-inflammatory cytokines. Plasma isolated from mouse peripheral blood was used for protein assay by Luminex with a 17-plex human cytokine kit. Results were expressed as mean±SD. The profile of different treatments was compared by means of a generalized estimating equation (GEE) model (*,p<0.0167; **,p<0.0033, for multiple comparisons).

In moderate GVHD, anti-CCL24 antibody or CXCL5 could effectively mimic the immunosuppressive effect of the 2F cocktail. It maintained mice 36-day survival at 78.3% (CXCL5: 18/23 mice) and 82.6% (anti-CCL24: 19/23 mice) with mild symptoms, while the 2F cocktail treatment maintained survival at 81.0% (17/21 mice) (FIGS. 9A and 9B). However, in severe GVHD, single factor lost its immunosuppressive capacity. Survival dropped to 26.1% (6/23 mice) and 16.7% (3/18 mice) with moderate symptoms when mice were treated with CXCL5 or anti-CCL24 antibody (FIGS. 9C and 9D). The results were significantly lower than in mice treated with the 2F cocktail (61.9%, 13/21 mice) ($p<0.05$). Cell population assay demonstrated that CXCL5 or anti-CCL24 antibody alone gave suboptimal immunosuppression effect on circulating CTLs, Th1 cells, splenic macrophages and NK cells (FIG. 10, A and B). This suggested that the two factors exhibit a concerted effect in severe GVHD. This is consistent with our in vitro observation that MSCs modulated immune reaction through multiple factors rather than through a single factor. It was also supported by the protein assay as CXCL5 was solely comparable to the 2F cocktail in the suppression of pro-inflammatory cytokines IFN-γ, IL-6, IL-8, and MIP-1β; while anti-CCL24 antibody was solely comparable in the suppression of IFN-γ, IL-6 and MIP-1β (FIG. 11).

The 2FC Treatment Attenuated SLE Symptoms and Prolonged the Mice Survival

The 2FC treatment attenuated SLE symptoms and prolonged the mice survival GVHD occurs when the graft rejects the host, whereas autoimmune disease is a condition arising from an abnormal immune response to a normal body part. The underlying principle is about alloimmunity in GVHD and autoimmunity in autoimmune disease. To some extent, they are sharing the same pathogenesis. Because of the profound immunosuppressive capacity in GVHD and the pathogenesis similarity, we intend to validate the pre-clinical efficacy of the 2FC in autoimmune diseases.

Figure 12:
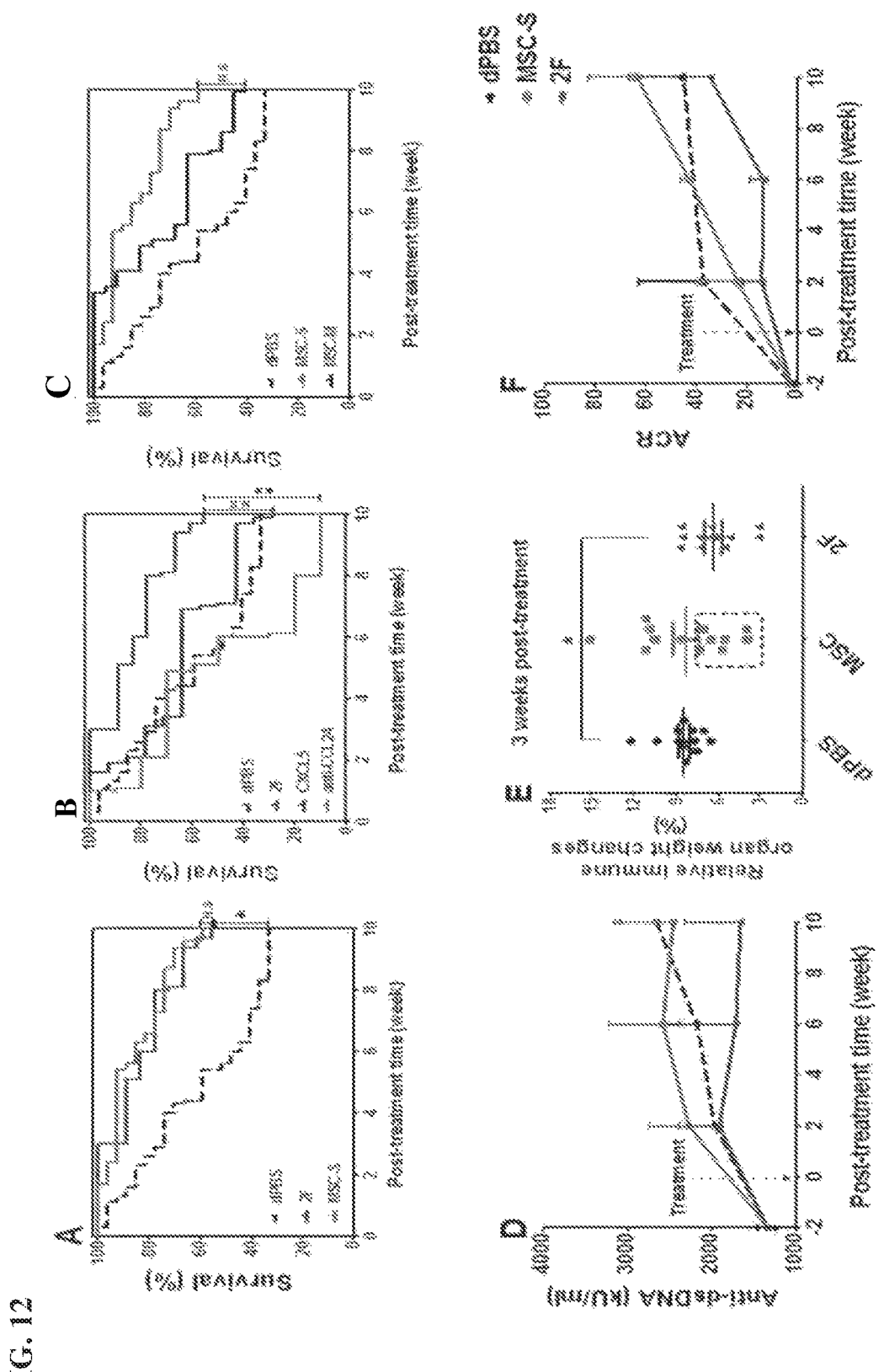
FIG. 12 provides data showing that the 2F cocktail treatment attenuated SLE symptoms and prolonged survival. (A) shows Kaplan-Meier survival curves in mice treated with standard mesenchymal stromal cell treatment (MSC) or 2F cocktail (n=4; $N_{dPBS}$=29 mice, $N_{2F}$=18 mice, $N_{MSC}$=18 mice). (B) shows Kaplan-Meier survival curves in mice treated with 2F cocktail or single factor ($N_{dPBS}$=29 mice, $N_{2F}$=18 mice, $N_{CXCL5}$=14 mice, $N_{anti-CCL24}$=10 mice). (C) shows Kaplan-Meier survival curves in mice treated with single or multiple MSC injection ($N_{dPBS}$=29 mice, $N_{MSC-S}$=18 mice, $N_{MSC-M}$=23 mice). From (A) to (C), the significance is calculated by log-rank test as *p<0.05; p<0.01; *p<0.001; N.S means no significant difference. (D) shows line graphs depicting data showing the plasma autoantibody concentration. Results were expressed as mean±SD. (E) shows dot plots depicting data showing the lymphoproliferation reduction in $Fas^{lpr}$ mice (*p<0.05). (F) shows line graphs depicting data showing the urine albumin-to-creatinine ratio in $Fas^{lpr}$ mice. Results were expressed as mean±SD. (G) shows lymphocyte infiltration in kidney by haematoxylin and eosin (H&E) staining. (H) to (J) The average number of mesenteric lymph node, spleen and thymic effector cells in $Fas^{lpr}$ mice after BM-MSCs and 2FC treatment. Results were expressed by scatter plot with mean value (*p<0.05; p<0.01; *p<0.001).
Figure 12:
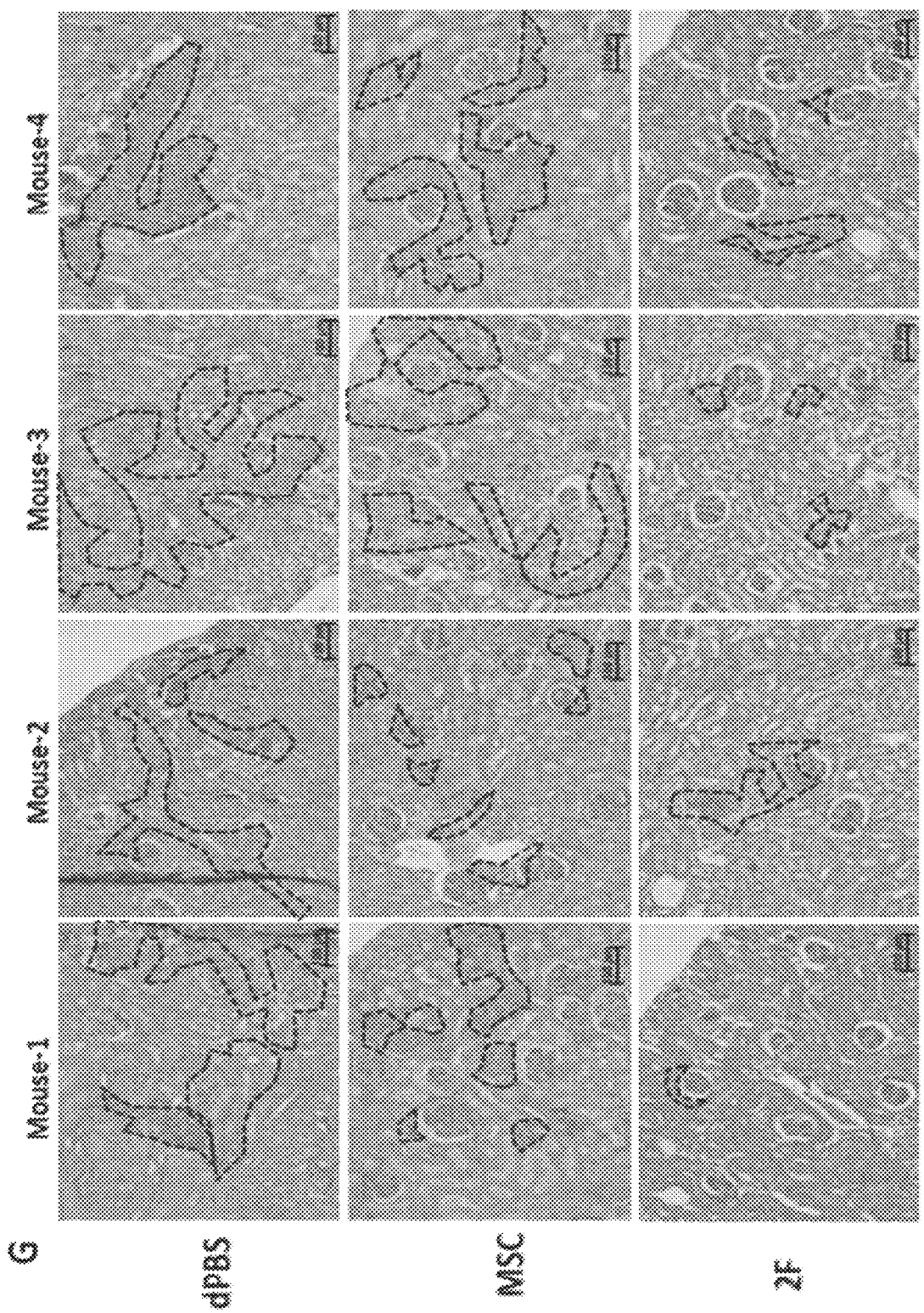
Figure 12:
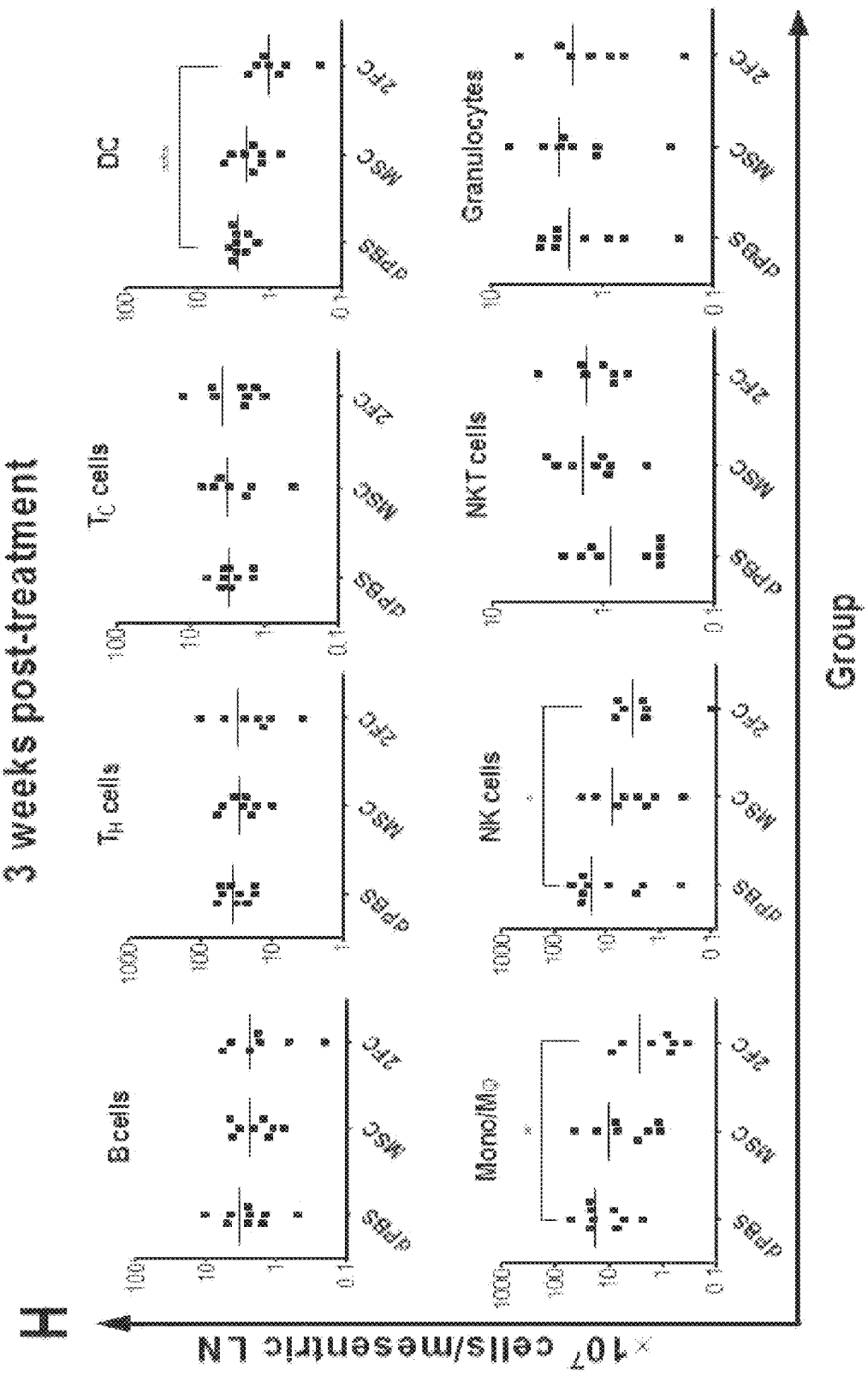
Figure 12:
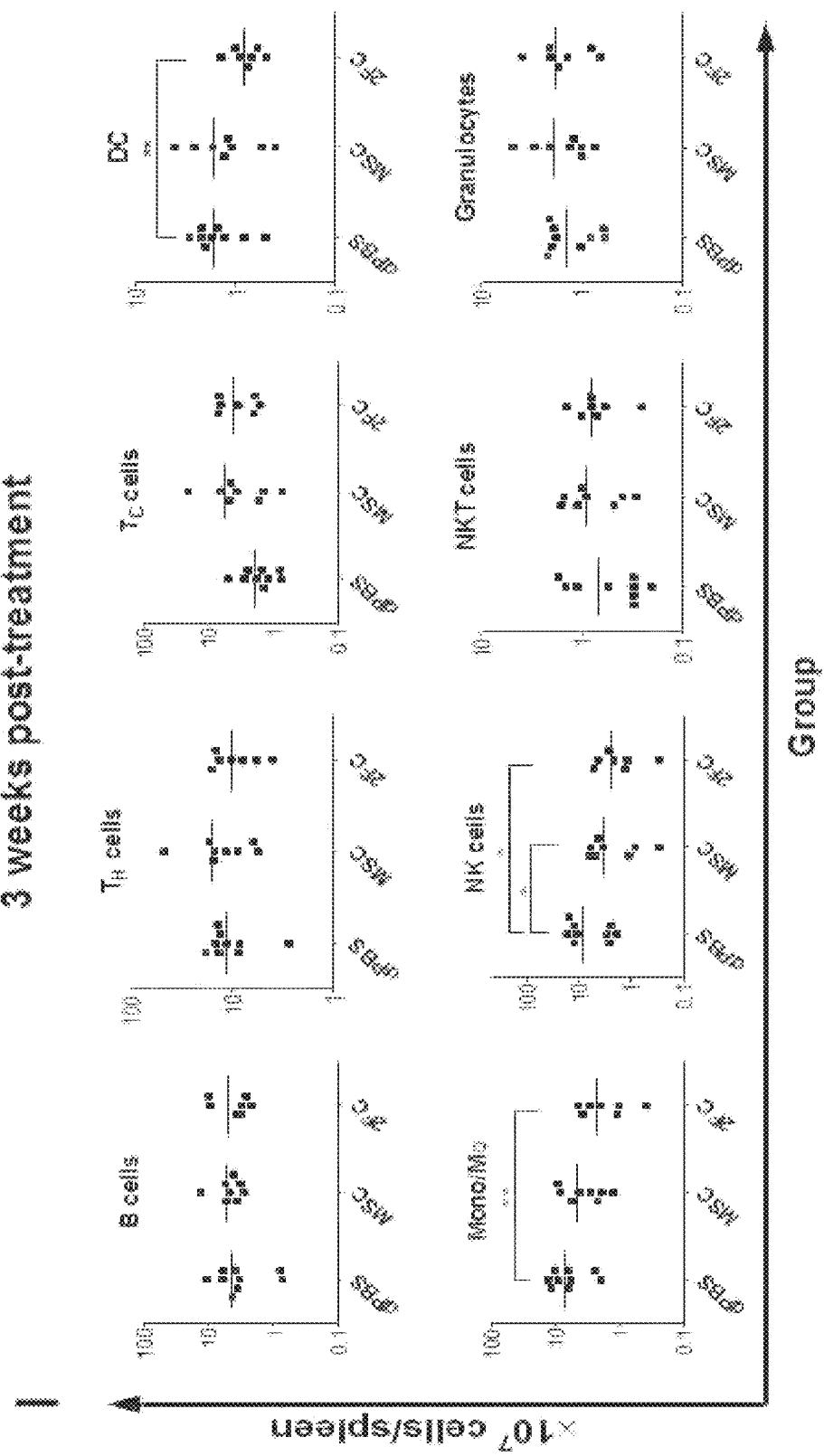
Figure 12:
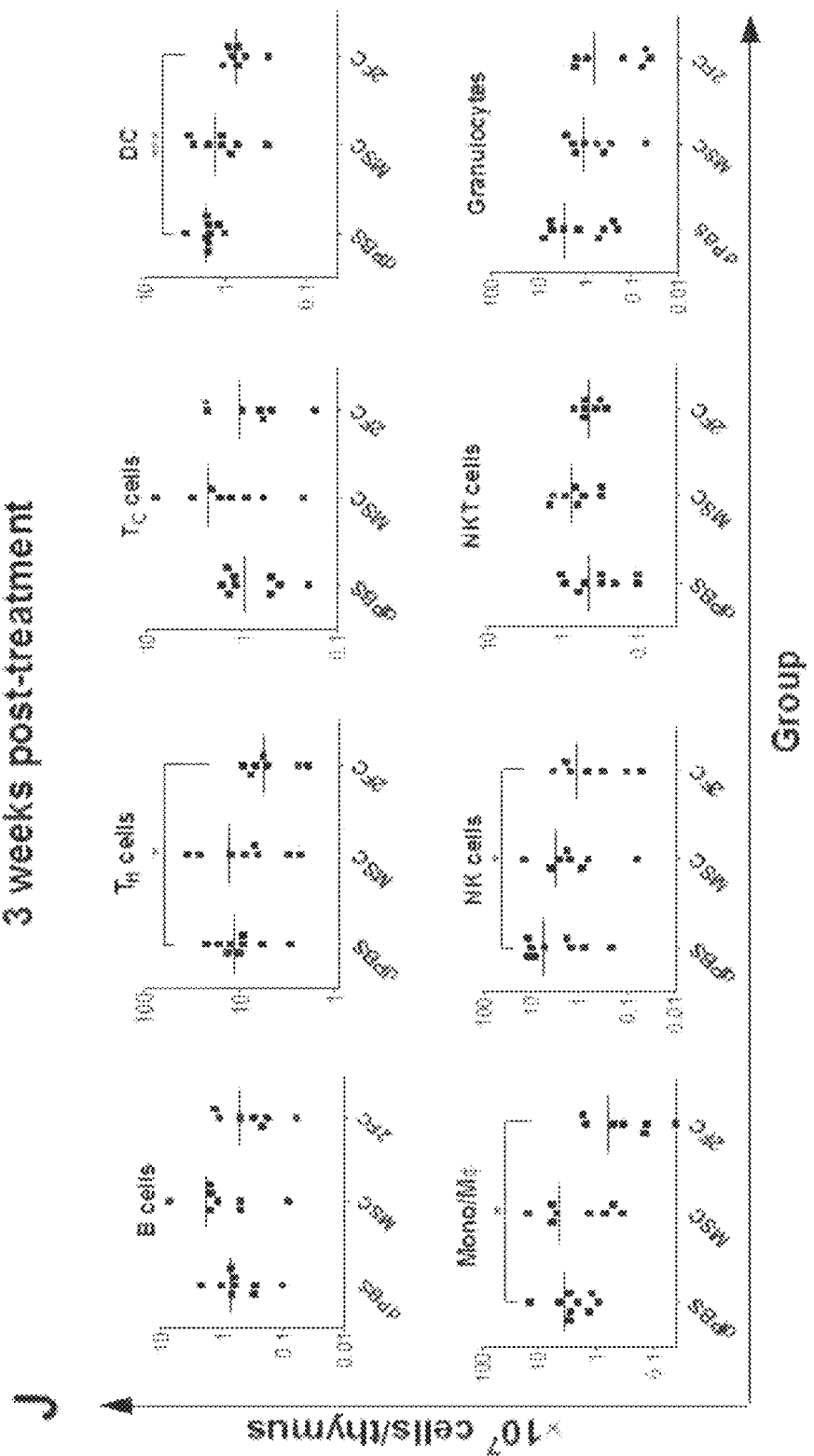

In SLE model, $Fas^{lpr}$ mice 10 weeks post-treatment survival was significantly improved from 33.3% (dPBS: 9/27 mice) to 55.6% (2FC: 10/18 mice, $p<0.05$), which was comparable to BM-MSCs treatment (59.3%, 16/27 mice) (FIG. 12, A). It was better than single factor CXCL5 (28.6%, 4/14 mice) or anti-CCL24 antibody (10%, 1/10 mice) treatment (FIG. 12, B, $p<0.05$). This result suggests that CXCL5 concerted with anti-CCL24 antibody to exert its immunosuppression function. In addition, In addition, single BM-MSC treatment was better than multiple BM-MSC (monthly) treatment (39.1%, 9/23 mice) even the significance was not achieved (FIG. 12, C). For autoantibody secretion including IgA, IgG and IgM, the 2FC treatment reduced its increasing rate. However, this phenomenon was not observed in BM-MSCs treatment (FIG. 12, D). The lymphoproliferation was reduced as the weight of mesenteric lymph node, spleen and thymus relative to its own body weight was reduced from 8.4% to 6.3% when mice were treated with the 2FC for 3 weeks ($p<0.05$). While this effect was only observed in part of $Fas^{lpr}$ mice when mice were treated with BM-MSCs (FIG. 12, E). Mice kidney function was improved as the 2FC treatment continuously slowed down the ACR increment during 10 weeks treatment period, while BM-MSCs treatment could only provide the short term protection for 4-5 weeks and then lost its kidney protection function (FIG. 12, F). This phenomenon was consistent with histological observation (FIG. 12, G). The massive lymphocytes infiltration was significantly reduced in mice treated with the 2FC, while just reduced in some mice those treated with BM-MSCs. The proliferation of effector cells, such as dendritic cells (DCs), monocytes/macrophages and natural killer cells (NK cells) were significantly suppressed in mesenteric lymph nodes (LN), thymus and spleen by the 2FC treatment (FIG. 12, H and I). Beyond that, helper T cells were also suppressed significantly in thymus (FIG. 12, J). These effects were more potent than those observed with BM-MSCs treatment.

TABLE 2

List of regulated proteins

| Cytokine | Relative expression (fold change) MLR on MSC MLR + MSC − CM |
|---|---|
| MIP-3-alpha (CCL20) | 29.79 ± 34.05 |
| MCP-3 (CCL8) | 4.93 ± 5.22 |
| ENA-78 (CXCL5) | 4.77 ± 1.90 |
| OPG | 4.21 ± 1.21 |
| GCP-2 (CXCL6) | 3.52 ± 5.53 |
| IL-1beta | 0.33 ± 0.23 |
| I-309 (CCL1) | 0.31 ± 0.25 |
| Eotaxin-2 (CCL24) | 0.17 ± 0.09 |

Results were expressed as mean ± S.E., n = 3

TABLE 3

Experimental condition in $2^{12}$ fractional FD

| Factor Condition | PGE2 | CCL20 | CXCL6 | CCL8 | CCL7 | OPG | IL-10 | CXCL5 | anti-CCL1 | anti-IL1b | anti-M-CSF | anti-CCL24 |
|---|---|---|---|---|---|---|---|---|---|---|---|---|
| C1 (MLR) | 1 | 1 | 1 | 1 | 1 | 1 | 1 | 1 | 1 | 1 | 1 | 1 |
| C2 | 1 | 1 | 1 | 1 | 1 | 1 | 1 | 2 (50 ng/ml) | 2 (2 μg/ml) | 2 (1 μg/ml) | 2 (1 μg/ml) | 2 (2 μg/ml) |
| C3 | 1 | 1 | 1 | 2 (10 ng/ml) | 2 (50 ng/ml) | 2 (10 ng/ml) | 2 (10 ng/ml) | 1 | 1 | 1 | 1 | 2 (2 μg/ml) |
| C4 | 1 | 1 | 1 | 2 (10 ng/ml) | 2 (50 ng/ml) | 2 (10 ng/ml) | 2 (10 ng/ml) | 2 (50 ng/ml) | 2 (2 μg/ml) | 2 (1 μg/ml) | 2 (1 μg/ml) | 1 |

TABLE 3-continued

Experimental condition in $2^{12}$ fractional FD

| Factor Condition | PGE2 | CCL20 | CXCL6 | CCL8 | CCL7 | OPG | IL-10 | CXCL5 | anti-CCL1 | anti-IL1b | anti-M-CSF | anti-CCL24 |
|---|---|---|---|---|---|---|---|---|---|---|---|---|
| C5 | 1 | 2 (50 ng/ml) | 2 (10 ng/ml) | 1 | 1 | 2 (10 ng/ml) | 2 (10 ng/ml) | 1 | 1 | 2 (1 μg/ml) | 2 (1 μg/ml) | 1 |
| C6 | 1 | 2 (50 ng/ml) | 2 (10 ng/ml) | 1 | 1 | 2 (10 ng/ml) | 2 (10 ng/ml) | 2 (50 ng/ml) | 2 (2 μg/ml) | 1 | 1 | 2 (2 μg/ml) |
| C7 | 1 | 2 (50 ng/ml) | 2 (10 ng/ml) | 2 (10 ng/ml) | 2 (50 ng/ml) | 1 | 1 | 1 | 1 | 2 (1 μg/ml) | 2 (1 μg/ml) | 2 (2 μg/ml) |
| C8 | 1 | 2 (50 ng/ml) | 2 (10 ng/ml) | 2 (10 ng/ml) | 2 (50 ng/ml) | 1 | 1 | 2 (50 ng/ml) | 2 (2 μg/ml) | 1 | 1 | 1 |
| C9 | 2 (2 μM) | 1 | 2 (10 ng/ml) | 1 | 2 (50 ng/ml) | 1 | 2 (10 ng/ml) | 1 | 2 (2 μg/ml) | 1 | 2 (1 μg/ml) | 1 |
| C10 | 2 (2 μM) | 1 | 2 (10 ng/ml) | 1 | 2 (50 ng/ml) | 1 | 2 (10 ng/ml) | 2 (50 ng/ml) | 1 | 2 (1 μg/ml) | 1 | 2 (2 μg/ml) |
| C11 | 2 (2 μM) | 1 | 2 (10 ng/ml) | 2 (10 ng/ml) | 1 | 2 (10 ng/ml) | 1 | 1 | 2 (2 μg/ml) | 1 | 2 (1 μg/ml) | 2 (2 μg/ml) |
| C12 | 2 (2 μM) | 1 | 2 (10 ng/ml) | 2 (10 ng/ml) | 1 | 2 (10 ng/ml) | 1 | 2 (50 ng/ml) | 1 | 2 (1 μg/ml) | 1 | 1 |
| C13 | 2 (2 μM) | 2 (50 ng/ml) | 1 | 1 | 2 (50 ng/ml) | 2 (10 ng/ml) | 1 | 1 | 2 (2 μg/ml) | 2 (1 μg/ml) | 1 | 1 |
| C14 | 2 (2 μM) | 2 (50 ng/ml) | 1 | 1 | 2 (50 ng/ml) | 2 (10 ng/ml) | 1 | 2 (50 ng/ml) | 1 | 1 | 2 (1 μg/ml) | 2 (2 μg/ml) |
| C15 | 2 (2 μM) | 2 (50 ng/ml) | 1 | 2 (10 ng/ml) | 1 | 1 | 2 (10 ng/ml) | 1 | 2 (2 μg/ml) | 2 (1 μg/ml) | 1 | 2 (2 μg/ml) |
| C16 | 2 (2 μM) | 2 (50 ng/ml) | 1 | 2 (10 ng/ml) | 1 | 1 | 2 (10 ng/ml) | 2 (50 ng/ml) | 1 | 1 | 2 (1 μg/ml) | 1 |
| Full panel | 2 (2 μM) | 2 (50 ng/ml) | 2 (10 ng/ml) | 2 (10 ng/ml) | 2 (50 ng/ml) | 2 (10 ng/ml) | 2 (10 ng/ml) | 2 (50 ng/ml) | 2 (2 μg/ml) | 2 (1 μg/ml) | 2 (1 μg/ml) | 2 (2 μg/ml) |
| MLR on MSC | 1 | 1 | 1 | 1 | 1 | 1 | 1 | 1 | 1 | 1 | 1 | 1 |

"1" indicates that the substance is not present; "2" indicates that the substance is present.

TABLE 4

Experimental condition in $2^7$ fractional FD

| Factor Condition | anti-CCL24 | IL-10 | OPG | CXCL5 | CXCL6 | anti-CCL1 | CCL20 |
|---|---|---|---|---|---|---|---|
| C 1 (MLR) | 1 | 1 | 1 | 1 | 1 | 1 | 1 |
| C17 | 1 | 1 | 1 | 2 (50 ng/ml) | 2 (10 ng/ml) | 2 (2 μg/ml) | 2 (50 ng/ml) |
| C18 | 1 | 2 (10 ng/ml) | 2 (10 ng/ml) | 1 | 1 | 2 (2 μg/ml) | 2 (50 ng/ml) |
| C19 | 1 | 2 (10 ng/ml) | 2 (10 ng/ml) | 2 (50 ng/ml) | 2 (10 ng/ml) | 1 | 1 |
| C20 | 2 (2 ug/ml) | 1 | 2 (10 ng/ml) | 1 | 2 (10 ng/ml) | 1 | 2 (50 ng/ml) |
| C21 | 2 (2 ug/ml) | 1 | 2 (10 ng/ml) | 2 (50 ng/ml) | 1 | 2 (2 μg/ml) | 1 |
| C22 | 2 (2 ug/ml) | 2 (10 ng/ml) | 1 | 1 | 2 (10 ng/ml) | 2 (2 μg/ml) | 1 |
| C23 | 2 (2 ug/ml) | 2 (10 ng/ml) | 1 | 2 (50 ng/ml) | 1 | 1 | 2 (50 ng/ml) |
| Full panel | 2 (2 ug/ml) | 2 (10 ng/ml) | 2 (10 ng/ml) | 2 (50 ng/ml) | 2 (10 ng/ml) | 2 (2 μg/ml) | 2 (50 ng/ml) |

"1" indicates that the substance is not present; "2" indicates that the substance is present.

TABLE 5

Experimental condition in $2^4$ full FD

| Factor Condition | anti-CCL1 | anti-CCL24 | OPG | CXCL5 |
|---|---|---|---|---|
| C1 (MLR) | 1 | 1 | 1 | 1 |
| C24 | 2 (2 ug/ml) | 1 | 1 | 1 |
| C25 | 1 | 2 (2 ug/ml) | 1 | 1 |
| C26 | 1 | 1 | 2 (10 ng/ml) | 1 |
| C27 | 1 | 1 | 1 | 2 (50 ng/ml) |
| C28 | 2 (2 ug/ml) | 2 (2 ug/ml) | 1 | 1 |

TABLE 5-continued

Experimental condition in $2^4$ full FD

| Factor Condition | anti-CCL1 | anti-CCL24 | OPG | CXCL5 |
|---|---|---|---|---|
| C29 | 2 (2 ug/ml) | 1 | 2 (10 ng/ml) | 1 |
| C30 | 2 (2 ug/ml) | 1 | 1 | 2 (50 ng/ml) |
| C31 | 1 | 2 (2 ug/ml) | 2 (10 ng/ml) | 1 |
| C32 | 1 | 2 (2 ug/ml) | 1 | 2 (50 ng/ml) |
| C33 | 1 | 1 | 2 (10 ng/ml) | 2 (50 ng/ml) |
| C34 | 2 (2 ug/ml) | 2 (2 ug/ml) | 2 (10 ng/ml) | 1 |
| C35 | 2 (2 ug/ml) | 2 (2 ug/ml) | 1 | 2 (50 ng/ml) |
| C36 | 2 (2 ug/ml) | 1 | 2 (10 ng/ml) | 2 (50 ng/ml) |
| C37 | 1 | 2 (2 ug/ml) | 2 (10 ng/ml) | 2 (50 ng/ml) |
| C38-Full panel | 2 (2 ug/ml) | 2 (2 ug/ml) | 2 (10 ng/ml) | 2 (50 ng/ml) |

"1" indicates that the substance is not present; "2" indicates that the substance is present.

TABLE 6

Dosage for MTD study

| Time Soluble factor | Week-1 | Week-2 | Week-3 | Week-4 |
|---|---|---|---|---|
| dPBS | 100 μl/mouse | 100 μl/mouse | 100 μl/mouse | 100 μl/mouse |
| anti-CCL24 | 1 μg/ml | 2 μg/ml | 6 μg/ml | |
| CXCL5 | 10 ng/ml | 50 ng/ml | 100 ng/ml | 200 ng/ml |

TABLE 7

Histological score in NSG mice

| | dPBS | 2FC | MSC | CsA | CXCL5 | Anti-CCL24 |
|---|---|---|---|---|---|---|
| Skin | | | | | | |
| Vacuolar change | mild | none | none | none | none | none |
| spongiosis | mild | none | none | none | none | none |
| Lymphocytic satelitosis number of cells | >10 (severe) | <5 (mild) | >5 (mod) | >5 (mod) | <5 (mild) | <5 (mild) |
| Small intestine | | | | | | |
| Apoptosis | mild to entire crypt loss (moderate) | 2/hpf (mild) | 4/hpf (mild) | 2/hpf(mild) | 1/hpf (mild) | 1/hpf(mild) |
| Lymphocytic inflammation | nil | mild | mild | mild | mild | mild to none |
| Intraepithelial lymphocytosis | nil | 2/50 epithelial cells (mild) | 4/50 epithelial cells(mod) | 3/50 epithelial cells (mod) | 2/50 epithelial cells(mild) | 1/50 epithelial cells (mild) |
| Kidney | | | | | | |
| Interstitial inflammation | severe | mild | mod | mild | mild | mod |
| Tubulitis | mod | mild | mod | mild | mild | mod |
| Arterial changes | mild (1 vessel) | none | none | none | none | none |
| Σscore | 13 | 6 | 10 | 8 | 6 | 8 |

Overall score and severity: Mild, 0-9; moderate, 10-18; Severe, 19-27.

Mod: moderate; hpf: high power field.

The invention claimed is:

1. A pharmaceutical composition comprising at least one antibody and at least one mesenchymal stromal cell-derived protein,
   wherein the antibody targets CCL24 (Eotaxin-2); and
   wherein the mesenchymal stromal cell-derived protein is CXCL5 (ENA-78).

2. The pharmaceutical composition of claim 1, wherein the antibody is present in a concentration of about 0.05 μg/ml to about 5 μg/ml.

3. The pharmaceutical composition of claim 2, wherein the antibody is present in a concentration of about 1 μg/ml or about 2 μg/ml.

4. The pharmaceutical composition of claim 1, wherein the mesenchymal stromal cell-derived protein is present in a concentration of about 0.5 ng/ml to about 75 ng/ml.

5. The pharmaceutical composition of claim 4, wherein the mesenchymal stromal cell-derived protein is present in a concentration of about 10 ng/ml or 50 ng/ml.

6. A kit comprising the pharmaceutical composition of claim 1.

* * * * *